US 6,453,246 B1

(12) United States Patent
Agrafiotis et al.

(10) Patent No.: US 6,453,246 B1
(45) Date of Patent: Sep. 17, 2002

(54) SYSTEM, METHOD, AND COMPUTER PROGRAM PRODUCT FOR REPRESENTING PROXIMITY DATA IN A MULTI-DIMENSIONAL SPACE

(75) Inventors: Dimitris K. Agrafiotis, Downingtown; Victor S. Labanov; Francis R. Salemme, both of Yardley, all of PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/073,845

(22) Filed: May 7, 1998

Related U.S. Application Data

(63) Continuation-in-part of application No. 08/963,872, filed on Nov. 4, 1997, now Pat. No. 6,295,514.
(60) Provisional application No. 60/030,187, filed on Nov. 4, 1996.

(51) Int. Cl.[7] ................................................ G06F 17/00
(52) U.S. Cl. ........................ 702/27; 702/32; 702/179; 382/225
(58) Field of Search .......................... 702/22, 27, 28, 702/30–32, 155, 159, 179, 181, FOR 105, FOR 104, FOR 131, FOR 115–FOR 119, FOR 132, FOR 134, FOR 139, FOR 145, FOR 170, FOR 171; 706/15, 20, 21; 707/6, 102; 703/12, 2; 700/266, 268; 345/149; 382/113, 155–160, 224, 226–228, 225

(56) References Cited

U.S. PATENT DOCUMENTS

| 4,773,099 A | * | 9/1988 | Bokser | 382/225 |
|---|---|---|---|---|
| 4,811,217 A | | 3/1989 | Tokizane et al. | 364/300 |
| 4,859,736 A | | 8/1989 | Rink | 525/54.1 |
| 4,908,773 A | | 3/1990 | Pantoliano et al. | 364/496 |
| 4,935,875 A | | 6/1990 | Shah et al. | 364/497 |
| 4,939,666 A | | 7/1990 | Hardman | 436/89 |
| 5,010,175 A | | 4/1991 | Rutter et al. | 530/334 |
| 5,025,388 A | | 6/1991 | Cramer, III et al. | 364/496 |
| 5,155,801 A | | 10/1992 | Lincoln | 395/22 |
| 5,167,009 A | | 11/1992 | Skeirik | 395/27 |

(List continued on next page.)

FOREIGN PATENT DOCUMENTS

| EP | 0 355 266 B1 | 6/1993 | B01J/19/00 |
|---|---|---|---|
| EP | 0 355 628 B1 | 11/1993 | G21F/9/00 |
| EP | 0 770 876 A1 | 5/1997 | G01N/33/68 |

(List continued on next page.)

OTHER PUBLICATIONS

Bellman, R.E., *Adaptive Control Processes*, Princeton University Press, Princeton, NJ (1961), entire book submitted.

(List continued on next page.)

*Primary Examiner*—Hal Wachsman
(74) *Attorney, Agent, or Firm*—Sterne, Kessler, Goldstein & Fox PLLC

(57) ABSTRACT

A system, method and computer program product for representing precise or imprecise measurements of similarity/dissimilarity (relationships) between objects as distances between points in a multi-dimensional space that represents the objects. Self-organizing principles are used to iteratively refine an initial (random or partially ordered) configuration of points using stochastic relationship/distance errors. The data can be complete or incomplete (i.e. some relationships between objects may not be known), exact or inexact (i.e. some or all of the relationships may be given in terms of allowed ranges or limits), symmetric or asymmetric (i.e. the relationship of object A to object B may not be the same as the relationship of B to A) and may contain systematic or stochastic errors. The relationships between objects may be derived directly from observation, measurement, a priori knowledge, or intuition, or may be determined indirectly using any suitable technique for deriving proximity (relationship) data.

52 Claims, 7 Drawing Sheets

U.S. PATENT DOCUMENTS

| | | | | |
|---|---|---|---|---|
| 5,181,259 A | * | 1/1993 | Rorvig | 382/225 |
| 5,240,680 A | | 8/1993 | Zuckerman et al. | 422/67 |
| 5,260,882 A | | 11/1993 | Blanco et al. | 364/499 |
| 5,265,030 A | | 11/1993 | Skolnick et al. | 364/496 |
| 5,270,170 A | | 12/1993 | Schatz et al. | 435/7.37 |
| 5,288,514 A | | 2/1994 | Ellman | 427/2 |
| 5,307,287 A | | 4/1994 | Cramer, III et al. | 364/496 |
| 5,323,471 A | * | 6/1994 | Hayashi | 382/158 |
| 5,331,573 A | | 7/1994 | Balaji et al. | 364/500 |
| 5,434,796 A | | 7/1995 | Weininger | 364/496 |
| 5,436,850 A | | 7/1995 | Eisenberg et al. | 364/496 |
| 5,442,122 A | | 8/1995 | Noda et al. | 564/426 |
| 5,463,564 A | | 10/1995 | Agrafiotis et al. | 364/496 |
| 5,499,193 A | | 3/1996 | Sugawara et al. | 364/500 |
| 5,519,635 A | | 5/1996 | Miyake et al. | 364/497 |
| 5,524,065 A | * | 6/1996 | Yagasahi | 382/226 |
| 5,526,281 A | | 6/1996 | Chapman et al. | 364/496 |
| 5,545,568 A | | 8/1996 | Ellman | 436/518 |
| 5,549,974 A | | 8/1996 | Holmes | 428/403 |
| 5,553,225 A | | 9/1996 | Perry | 395/157 |
| 5,565,325 A | | 10/1996 | Blake | 435/7.1 |
| 5,574,656 A | | 11/1996 | Agrafiotis et al. | 364/500 |
| 5,585,277 A | | 12/1996 | Bowie et al. | 436/518 |
| 5,598,510 A | | 1/1997 | Castelaz | 395/23 |
| 5,602,755 A | | 2/1997 | Ashe et al. | 364/498 |
| 5,602,938 A | * | 2/1997 | Akiyama et al. | 382/155 |
| 5,612,895 A | | 3/1997 | Balaji et al. | 364/496 |
| 5,634,017 A | | 5/1997 | Mohanty et al. | 395/326 |
| 5,635,598 A | | 6/1997 | Lebl et al. | 530/334 |
| 5,670,326 A | | 9/1997 | Beutel | 435/7.1 |
| 5,679,582 A | | 10/1997 | Bowie et al. | 436/518 |
| 5,684,711 A | | 11/1997 | Agrafiotis et al. | 364/500 |
| 5,703,792 A | | 12/1997 | Chapman | 364/496 |
| 5,712,171 A | | 1/1998 | Zambias et al. | 436/518 |
| 5,712,564 A | | 1/1998 | Hayosh | 324/210 |
| 5,734,796 A | | 3/1998 | Pao | 395/22 |
| 5,736,412 A | | 4/1998 | Zambias et al. | 436/518 |
| 5,740,326 A | * | 4/1998 | Boulet et al. | 382/158 |
| 5,789,160 A | | 8/1998 | Eaton et al. | 435/6 |
| 5,807,754 A | | 9/1998 | Zambias et al. | 436/518 |
| 5,811,241 A | | 9/1998 | Goodfellow et al. | 435/7.1 |
| 5,832,494 A | | 11/1998 | Egger et al. | 707/102 |
| 5,845,225 A | | 12/1998 | Mosher | 701/102 |
| 5,858,660 A | | 1/1999 | Eaton et al. | 435/6 |
| 5,861,532 A | | 1/1999 | Brown et al. | 564/142 |
| 5,866,334 A | | 2/1999 | Beutel | 435/6 |
| 5,901,069 A | | 5/1999 | Agrafiotis et al. | 364/528.03 |
| 5,908,960 A | | 6/1999 | Newlander | 564/177 |
| 5,933,819 A | | 8/1999 | Skolnick et al. | 706/21 |
| 5,960,443 A | | 9/1999 | Young et al. | 707/104 |
| 5,995,938 A | | 11/1999 | Whaley | 705/3 |
| 6,014,661 A | | 1/2000 | Ahlberg et al. | 707/3 |
| 6,026,397 A | | 2/2000 | Sheppard | 707/5 |
| 6,037,135 A | | 3/2000 | Kubo et al. | 435/7.24 |
| 6,049,797 A | | 4/2000 | Guha et al. | 707/6 |

FOREIGN PATENT DOCUMENTS

| | | | | |
|---|---|---|---|---|
| EP | 0 818 744 A2 | 1/1998 | | G06F/17/50 |
| WO | WO 91/19735 | 12/1991 | | C07K/7/02 |
| WO | WO 92/00091 | 1/1992 | | A61K/37/02 |
| WO | WO 93/20242 | 10/1993 | | C12Q/1/70 |
| WO | WO 94/28504 | 12/1994 | | G06F/15/60 |
| WO | WO 95/01606 | 1/1995 | | G06F/15/42 |
| WO | WO 97/09342 | 3/1997 | | C07H/21/02 |
| WO | WO 97/20952 | 6/1997 | | C12Q/1/68 |
| WO | WO 97/27559 | 7/1997 | | G06F/19/00 |
| WO | WO 98/20437 | 5/1998 | | G06F/17/50 |
| WO | WO 98/20459 | 5/1998 | | G06T/11/20 |

OTHER PUBLICATIONS

Bezdek, J.C., *Pattern Recognition with Fuzzy Objective Function Algorithms,* Plenum Press, New York, NY (1981), entire book submitted.

Hosenpud, J.D. et al, "The Effect of Transplant Center Volume on Cardiac Transplant Outcome," *The Journal of the American Medical Association,* vol. 271, No. 23, Jun. 1994, pp. 1844–1849.

Jain et al., "Artificial Neural Networks: A Tutorial," *Computer,* IEEE, Mar. 1996, pp. 31–44.

Johnson, M.A. and Maggiora, G.M., *Concepts and Applications of Molecular Similarity,* John Wiley and Sons, New York, NY (1990), entire book submitted. (No Month).

Kohonen, T., *Self–Organizing Maps,* Springer–Verlag, Heidelberg, Germany (1995), entire book submitted. (No Month).

Oja, E., *Subspace Methods of Pattern Recognition,* Research Studies Press, Letchworth, England (1983), entire book submitted. (No Month).

Porto et al., "Alternative Neural Network Training Methods," *IEEE Expert,* Jun. 1995, pp. 16–22.

Agrafiotis, D.K., "A New Method For Analyzing Protein Sequence Relationships Based On Sammon Maps," *Protein Science,* Cambridge University Press, vol. 6, No. 2, Feb. 1997, pp. 287–293.

Borg, Inger and Groenen, Patrick, *Modern Multidimensional Scaling Theory and Applications,* Springer Series in Statistics, Springer–Verlag, 1997, entire book submitted.

Agrafiotis, D.K. et al., "Advances in diversity profiling and combinatorial series design," *Molecular Diversity,* Kluwers/Escom, vol. 4, 1999, pp. 1–22. (No Month).

Agrafiotis, D.K. and Lobanov, V.S., "An Efficient Implementation of Distance–Based Diveristy Measure based on k–d Trees," *J. Chem. Inf. Comput. Sci.,* American Chemical Society, vol. 39, No. 1, Jan./Feb. 1999, pp. 51–58.

Agrafiotis, D.K. and Lobanov, V.S., "Bridging The Gap Between Diversity And QSAR," *Abstracts of Papers Part 1: 215th ACS National Meeting,* American Chemical Society, Mar. 28–Apr. 2, 1998, p. 181–COMP.

Agrafiotis, D.K. and Jaeger, E.P., "Directed Diversity®: An Operating System For Combinatorial Chemistry," *Abstracts of Papers Part 1: 211th ACS National Meeting,* American Chemical Society, Mar. 24–28, 1996, p. 46–COMP.

Agrafiotis, D.K., "Diversity of Chemical Libraries," *Encyclopedia of Computational Chemistry,* John Wiley & Sons, vol. 1:A–D, 1998, pp. 742–761. (No Month).

Agrafiotis, D.K., "On the Use of Information Theory for Assessing Molecular Diversity," *J. Chem. Inf. Comput. Sci.,* American Chemical Society, vol. 37, No. 3, May/Jun. 1997, pp. 576–580.

Agrafiotis, D.K. et al., "Parallel QSAR," *Abstracts of Papers Part 1: 217th ACS National Meeting,* American Chemical Society, Mar. 21–25, 1999, p. 50–COMP.

Agrafiotis, D.K. et al., "PRODEN: A New Program for Calculating Integrated Projected Populations," *Journal of Computational Chemistry,* John Wiley & Sons, vol. 11, No. 9, Oct. 1990, pp. 1101–1110.

Agrafiotis, D.K. and Jaeger, E.P., "Stochastic Algorithms for Exploring Molecular Diversity," *Abstracts of Papers Part 1: 213th ACS National Meeting,* American Chemical Society, Apr. 13–17, 1997, p. 16–CINF.

Agrafiotis, D., "Theoretical Aspects of the Complex: Arts and New Technologies," *Applications and Impacts Information Processing '94,* Elsevier Science, vol. II, 1994, pp. 714–719. (No Month).

Biswas, G. et al., "Evaluation of Projection Algorithms," *IEEE Transactions On Pattern Analysis And Machine Intelligence,* IEEE Computer Society, vol. PAMI–3, No. 6, Nov. 1981, pp. 701–708.

Bonchev, D. and Trinajstić, N., "Information theory, distance matrix, and molecular branching," *The Journal of Chemical Physics,* American Institute of Physics, vol. 67, No. 10, Nov. 15, 1977, pp. 4517–4533.

Chang, C.L. and Lee, R.C.T., "A Heuristic Relaxation Method for Nonlinear Mapping in Cluster Analysis," *IEEE Transactions on Systems, Man, and Cybernetics,* IEEE Systems, Man, and Cybernetics Society, vol. SMC–3, Mar. 1973, pp. 197–200.

Cramer, R.D. et al., "Virtual Compound Libraries: A New Approach to Decision Making in Molecular Discovery Research," *J. Chem. Inf. Comput. Sci.,* American Chemical Society, vol. 38, No. 6, Nov./Dec. 1998, pp. 1010–1023.

DeMers, D. and Cottrell, G., "Non–Linear Dimensionality Reduction," *Advances in Neural Information Processing Systems,* vol. 5, 1993, pp. 580–587.

Frey, P.W. and Slate, D.J., "Letter Recognition Using Holland–Style Adaptive Classifiers," *Machine Learning,* Kluwer Academic Publishers, vol. 6, 1991, pp. 161–182.

Friedman, J.H., "Exploratory Projection Pursuit," *Journal of the American Statistical Association,* American Statistical Association, vol. 82, No. 397, Mar. 1987, pp. 249–266.

Friedman, J.H. and Tukey, J.W., "A Projection Pursuit Algorithm for Exploratory Data Analysis," *IEEE Transactions on Computers,* IEEE Computer Society, vol. C–23, No. 9, Sep. 1974, pp. 881–889.

Garrido, L. et al., "Use of Multilayer Feedforward Neural Nets As A Display Method for Multidimensional Distributions," *International Journal of Neural Systems,* World Scientific Publishing Company, vol. 6, No. 3, Sep. 1995, pp. 273–282.

Ghose, A.K. et al., "Prediction of Hydrophobic (Lipophilic) Properties of Small Organic Molecules Using Fragmental Methods: An Analysis of ALOGP and CLOGP Methods," *J. Phys. Chem. A,* American Chemical Society, vol. 102, No. 21, May 21, 1998, pp. 3762–3772.

Hall, L.H. and Kier, L.B., "The Molecular Connectivity Chi Indexes and Kappa Shape Indexes in Structure–Property Modeling," *Reviews in Computational Chemistry: Advances,* VCH Publishers, 1991, pp. 367–422. (No Month).

Hecht–Nielsen, R., "Replicator Neural Networks for Universal Optimal Source Coding," *Science,* American Chemical Association for the Advancement of Science, vol. 269, Sep. 29, 1995, pp. 1860–1863.

Hotelling, H., "Analysis of a Complex of Statistical Variables into Principal Components," *The Journal of Educational Psychology,* Warwick and York, Inc., vol. XXIV, No. 6, Sep. 1933, pp. 417–441.

Hotelling, H., "Analysis of a Complex of Statistical Variables into Principal Components," *The Journal of Educational Psychology,* Warwick and York, Inc., vol. XXIV, No. 7, Oct. 1933, pp. 498–520.

Lee, R.C.T. et al., "A Triangulation Method for the Sequential Mapping of Points from N–Space to Two–Space," *IEEE Transactions on Computers,* IEEE Computer Society, Mar. 1977, pp. 288–292.

Lipinski, C.A. et al., "Experimental and computational approaches to estimate solubility and permeability in drug discovery and development settings," *Advanced Drug Delivery Reviews,* Elsevier Science B.V., vol. 23, 1997, pp. 3–25. (No Month).

Lobanov, V.S. and Agrafiotis, D.K., "Intelligent Database Mining Techniques," *Abstracts of Papers Part 1: 215th ACS National Meeting,* American Chemical Society, Mar. 29–Apr. 2, 1998, p. 19–COMP.

Lobanov, V.S. et al., "Rational Selections from Virtual Libraries," *Abstracts of Papers Part 1: 217th ACS National Meeting,* American Chemical Society, Mar. 21–25, 1999, p. 181–COMP.

Mao, J. and Jain, A.K., "Artificial Neural Networks for Feature Extraction and Multivariate Data Projection," *IEEE Transactions on Neural Networks,* IEEE Neural Networks Council, vol. 6, No. 2, Mar. 1995, pp. 296–317.

Oja, E., "Principal Components, Minor Components, and Linear Neural Networks," *Neural Networks,* Pergamon Press, vol. 5, 1992, pp. 927–935. (No Month).

Patterson, D.E. et al., "Neighborhood Behavior: A Useful Concept for Validation of 'Molecular Diversity' Descriptors," *Journal of Medicinal Chemistry,* American Chemical Society, vol. 39, No. 16, 1996, pp. 3049–3059. (No Month).

Pykett, C.E., "Improving the Efficiency of Sammon's Nonlinear Mapping by Using Clustering Archetypes," *Electronics Letters,* IEE, vol. 14, No. 25, Dec. 7, 1978, pp. 799–800.

Rubner, J. and Tavan, P., "A Self–Organizing Network for Principal–Component Analysis," *Europhysics Letters,* European Physical Society, vol. 10, No. 7, Dec. 1, 1989, pp. 693–698.

Sadowski, J. et al., "Assessing Similarity and Diversity of Combinatorial Libraries by Spatial Autocorrelation Functions and Neural Networks," *Angewandte Cheme,* Gessellschaft Deutscher Chemiker, vol. 34, No. 23/24, Jan. 5, 1996, pp. 2674–2677.

Thompson, L.A. and Ellman, J.A., "Synthesis and Applications of Small Molecule Libraries," *Chemical Reviews,* American Chemical Society, vol. 96, No. 1, Jan./Feb. 1996, pp. 555–600.

Barnard, John M. and Downs, Geoff M., "Computer representation and manipulation of combinatorial libraries," *Perspectives in Drug Discovery and Design,* Kluwer/Escom, 1997, pp. 13–30. (No Month).

Brint, Andrew T. and Willett, Peter, "Upperbound procedures for the identification of similar three–dimensional chemical structures," *Journal of Computer–Aided Molecular Design,* Escom, vol. 2, No. 4, 1988, pp. 311–320. (No Month).

Brown, Robert D. and Martin, Yvonne C., "Designing Combinatorial Library Mixtures Using a Genetic Algorithm," *Journal of Medicinal Chemistry,* American Chemical Society, vol. 40, No. 15, 1997, pp. 2304–2313. (No Month).

Gasteiger, J. et al., "Analysis of the Reactivity of Single Bonds in Aliphatic Molecules by Statistical and Pattern Recognition Methods," *Journal of Chemical Information Computer Science,* American Chemical Society, vol. 33, No. 3, 1993, pp. 385–394. (No Month).

Gillet, Valerie J. et al., "The Effectiveness of Reactant Pools for Generating Structurally–Diverse Combinatorial Libraries," *Journal of Chemical Information Computer Sciences,* American Chemical Society, vol. 37, No. 4, 1997, pp. 731–740. (No Month).

Gillet, Valerie J. et al., "Selecting Combinatorial Libraries to Optimize Diversity and Physical Properties," *Journal of Chemical Information Computer Sciences,* American Chemical Society, vol. 39, No. 1, 1999, pp. 169–177. (No Month).

Guez, Allon and Nevo, Igal, "Neural networks and fuzzy logic in clinical laboratory computing with application to integrated monitoring," *Clinica Chimica Acta 248,* Elsevier Science B.V., 1996, pp. 73–90. (No Month).

Kearsley, Simon K. et al., "Chemical Similarity Using Physiochemical Property Descriptors," *Journal of Chemical Information Computer Science,* American Chemical Society, vol. 36, No. 1, 1996, pp. 118–127. (No Month).

Leland, Burton A. et al., "Managing the Combinatorial Explosion," *Journal of Chemical Information Computer Science,* American Chemical Society, vol. 37, No. 1, 1997, pp. 62–70. (No Month).

Lewis, Richard A. et al., "Similarity Measures for Rational Set Selection and Analysis of Combinatorial Libraries: The Diverse Property–Derived (DPD) Approach," *Journal of Chemical Information Computer Science,* American Chemical Society, vol. 37, No. 3, 1997, pp. 599–614. (No Month).

Martin, Eric J. and Critchlow, Roger E., "Beyond Mere Diversity: Tailoring Combinatorial Libraries for Drug Discovery," *Journal of Combinatorial Chemistry,* American Chemical Society, vol. 1, No. 1, 1999, pp. 32–45. (No Month).

Sen, K. (ed.), *Molecular Similarity I,* Springer–Verlag, 1995, pp. 1–30. (No Month).

Sheridan, Robert P. et al., "Chemical Similarity Using Geometric Atom Pair Descriptors," *Journal of Chemical Information Computer Science,* American Chemical Society, vol. 36, No. 1, 1996, pp. 128–136. (No Month).

Willett, Peter et al., "Chemical Similarity Searching," *Journal of Chemical Information Computer Science,* American Chemical Society, vol. 38, No. 6, 1998, pp. 983–996. (No Month).

Gasteiger et al, "Assessment of the Diversity of Combinatorial Libraries by an Encoding of Melcular Surface properties," *Abstracts of Papers, American Chemical Society,* American Chemical Society, 211th ACS National Meeting, Item 070, Mar. 1996. (Abstract Only).

Hassan, Moises et al., "Optimization and visualization of molecular diversity of combinatorial libraries," *Molecular Diversity,* Escom, 1996, vol. 2, pp. 64–74. (No Month).

de Ridder, D. and Duin, R.P.W., "Sammon's mapping using neural networks: A comparison," *Pattern Recognition Letters,* Elsevier Science B.V., vol. 18, No. 11–13, 1997, pp. 1307–1316. (No Month).

Kim, H. et al., "Self–Organized Distributed Networks for Learning Highly Nonlinear Mapping," *Intelligent Engineering Systems Through Artificial Neural Networks,* vol. 4, Nov. 13–16, 1994, pp. 109–114.

Pal, N.R. and Eluri, V.K., "Two Efficient Connectionist Schemes for Structure Preserving Dimensionality Reduction," *IEEE Transactions on Neural Networks,* IEEE, vol. 9, No. 6, Nov. 1998, pp. 1142–1154.

Amzel, L.M., "Structure–based drug design," *Current Opinion in Biotechnology,* vol. 9, No. 4, Aug. 1998, pp. 366–369.

Blaney, J.M. and Martin, E.J., "Computational approaches for combinatorial library design and molecular diversity analysis," *Current Opinion in Chemical Biology,* vol. 1, No. 1, Jun. 1997, pp. 54–59.

Brown, R.D. and Clark, D.E., "Genetic diversity: applications of evolutionary algorithms to combinatorial library design," *Expert Opinion on Therapeutic Patents,* vol. 8, No. 11, Nov. 1998, pp. 1447–1459.

Caflisch, A. and Karplus, M., "Computational combinatorial chemistry for de novo ligand design: Review and assessment," *Perspectives in Drug Discovery and Design,* vol. 3, 1995, pp. 51–84. (No Month).

Danheiser, S.L., "Current Trends in Synthetic Peptide and Chemical Diversity Library Design," *Genetic Engineering News,* May 1, 1994, pp. 10 and 31.

Eichler, U. et al., "Addressing the problem of molecular diversity," *Drugs of the Future,* vol. 24, No. 2, 1999, pp. 177–190.

Felder, E.R. and Poppinger, D., "Combinatorial Compound Libraries for Enhanced Drug Discovery Approaches," *Advances in Drug Research,* vol. 30, 1997, pp. 112–199. (No Month).

Geysen, H.M. and Mason, T.J., "Screening Chemically Synthesized Peptide Libraries for Biologically–Relevant Molecules," *Biorganic & Medicinal Chemistry Letters,* vol. 3, No. 3, 1993, pp. 397–404. (No Month).

Gobbi, A. et al., "New Leads By Selective Screening of Compounds From Large Databases," *Abstracts for CINF sponsored symposia,* Apr. 17, 1997, p. 22.

Grayhill, T.L. et al., "Enhancing the Drug Discovery Process by Integration of High–Throughput Chemistry and Structure–Based Drug Design," from *Molecular Diversity and Combinatorial Chemistry: Libraries and Drug Discovery,* Chaiken and Janda (eds.), American Chemical Society, 1996, pp. 16–27. (No Month).

Houghten, R.A. et al., "The Use of Synthetic Peptide Combinatorial Libraries for the Identification of Bioactive Peptides," *Peptide Research,* vol. 5, No. 6, 1992, pp. 351–358. (No Month).

Klopman, G., "Artificial Intelligence Approach to Structure-Activity Studies. Computer Automated Structure Evaluation of Biological Activity of Organic Molecules," *J. Am. Chem. Soc.,* vol. 106, No. 24, Nov. 28, 1984, pp. 7315–7321.

Lajiness, M.S. et al., "Implementing Drug Screening Programs Using Molecular Similarity Methods," *QSAR: Quantitative Structure–Activity Relationships in Drug Design,* 1989, pp. 173–176. (No Month).

Loew, G.H. et al., "Strategies for Indirect Computer–Aided Drug Design," *Pharmaceutical Research,* vol. 10, No. 4, 1993, pp. 475–486.

Lynch, M.F. et al., "Generic Structure Storage and Retrieval," *J. Chem. Inf. Comput. Sci.,* vol. 25, No. 3, Aug. 1985, pp. 264–270.

Myers, P.L. et al., "Rapid, Reliable Drug Discovery," *Today's Chemist At Work,* Jul./Aug. 1997, pp. 47–48, 51 & 53.

Pabo et al., "Computer–Aided Model Building Strategies for Protein Design," *Biochemistry,* vol. 25, No. 20, 1986, pp. 5987–5991. (No Month).

Saudek et al., "Solution Conformation of Endothelin–1 by H NMR, CD, and Molecular Modeling," *International Journal of Peptide Protein Res.,* vol. 37, No. 3, 1991, pp. 174–179. (No Month).

Saund, E., "Dimensionality–Reduction Using Connectionist Networks," *IEEE Transactions on Pattern Analysis and Machine Intelligence*, vol. 11, No. 3, Mar. 1989, pp. 304–314.

Singh, J. et al., "Application of Genetic Algorithms to Combinatorial Synthesis: A Computational Approach to Lead Identification and Lead Optimization," *J. Am. Chem. Soc.*, vol. 118, No. 7, Feb. 21, 1996, pp. 1669–1676.

Van Drie, J.H. and Lajiness, M.S., "Approaches to virtual library design," *Drug Discovery today*, vol. 3, No. 6, Jun. 1998, pp. 274–283.

Walters, W.P. et al., "Virtual screening—an overview," *Drug Discovery today*, vol. 3, No. 4, Apr. 1998, pp. 160–178.

Weber, L., "Evolutionary combinatorial chemistry: application of genetic algorithms," *Drug Discovery today*, vol. 3, No. 8, Aug. 1998, pp. 379–385.

Weber, L. et al., "Optimization of the Biological Activity of Combinatorial Compound Libraries by a Genetic Algorithm," *Angewandte Chemie International Edition in English*, vol. 34, No. 20, 1995, pp. 2280–2282. (No Month).

"3DP gains drug research patent", vol. 32, No. 1, Jan. 1996, 2 pages.

"Accelerate the Discovery Cycle with Chem–X!", 2 pages. (No Date).

Agrafiotis, D. K., et al., "Stochastic Algorithms for Maximizing Molecular Diversity", *Journal of Chemical Information and Computer Sciences*, vol. 37, pp. 841–851, (1997). (No Month).

Alsberg, B.K. et al., "Classification of pyrolysis mass spectra by fuzzy multivariate rule induction–comparison with regression, K–nearest neighbour, neural and decision–tree methods", *Analytica Chimica Acta*, vol. 348, No. 1–3, pp. 389–407, (Aug. 20, 1997).

Andrea, T.A. et al., "Applications of Neural Networks in Quantitative Structure–Activity Relationships of Dihydrofolate Reductase Inhibitors", *Journal of Medicinal Chemistry*, vol. 34, No. 9, pp. 2824–2836, (1991). (No Month).

Aoyama, T. et al., "Neural Networks Applied to Quantitative Structure–Activity Relationship Analysis", *Journal of Medicinal Chemistry*, vol. 33, No. 9, pp. 2583–2590, (1990). (No Month).

Aoyama, T. and Hiroshi Ichikawa, "Obtaining the Correlation Indices between Drug Activity and Structural Parameters Using a Neural Network", *Chemical & Pharmaceutical Bulletin*, vol. 39, No. 2, pp. 372–378, (1991). (No Month).

"ArQule Inc", from http://www.bioportfolio.com/arqule/products.htm, 5 pages, (Mar. 18, 1998).

Baum, R.M., "Combinatorial Approaches Provide Fresh Leads for Medicinal Chemistry", *Chemical & Engineering News*, Feb. 7, 1994, (pp. 20–26).

Bentley, J. L., "Multidimensional Binary Search Trees Used for Associative Searching", *Communications of the ACM*, vol. 18, No. 9, pp. 509–517, (Sep. 1975).

Bottou, L. and Vladimir Vapnik, "Local Learning Algorithms", *Neural Computation*, vol. 4, No. 6, pp. 888–900, (Nov. 1992).

Boulu, L.G. and Gordon M. Crippen, "Voronoi Binding Site Models: Calculation of Binding Modes and Influence of Drug Binding Data Accuracy", *Journal of Computational Chemistry*, vol. 10, No. 5, pp. 673–682, (1989). (No Month).

Boulu, L.G. et al., "Voronoi Binding Site Model of a Polycyclic Aromatic Hydrocarbon Binding Protein", *Journal of Medicinal Chemistry*, vol. 33, No. 2, pp. 771–775, (1990). (No Month).

Brown, R. D. and Yvonne C. Martin, "Use of Structure–Activity Data To Compare Structure–Based Clustering Methods and Descriptors for Use in Compound Selection", *Journal of Chemical Information and Computer Sciences*, vol. 36, No. 3, pp. 572–584, (1996). (No Month).

Cacoullos, T., "Estimation of a Multivariate Density", *Annals of The Institute of Statistical Mathematics*, vol. 18, No. 2, pp. 179–189, (1966). (No Month).

Clark, R.D., "OptiSim: An Extended Dissimilarity Selection Method for Finding Diverse Representative Subsets", *Journal of Chemical Information and Computer Sciences*, vol. 37, No. 6, pp. 1181–1188 (12 Page Internet printout), 1997. (No Month).

Clark, D. E., and David R. Westhead, "Evolutionary algorithms in computer–aided molecular design", *Journal of Computer–Aided Molecular Design*, vol. 10, No. 4, pp. 337–358, (Aug. 1996).

Cramer, R. D. III et al., "Comparative Molecular Field Analyisis (CoMFA). 1. Effect of Shape on Binding of Steroids to Carrier Proteins", *Journal of The American Chemical Society*, vol. 110, No. 18, pp. 5959–5967, (Aug. 31, 1988).

Cramer, R. D. III et al., "Substructural Analysis. A Novel Approach to the Problem of Drug Design", *Journal of Medicinal Chemistry*, vol. 17, No. 5, pp. 533–535, (May 1974).

Crippen, G. M., "Voronoi binding Site Models", *Journal of Computational Chemistry*, vol. 8, No. 7, pp. 943–955, (Oct./Nov. 1987).

Friedman, J. H. et al., "An Algorithm for Finding Best Matches in Logarithmic Expected Time", *ACM Transactions on Mathematical Software*, vol. 3, No. 3, pp. 209–226, (Sep. 1977).

Friedman, J.H., "Fitting Functions To Noisy Data In High Dimensions", Department of Statistics—Stanford University Technical Report No. 101, (Aug., 1988), pp. 1–42.

Gallop, M. A. et al., "Applications of Combinatorial Technologies to Drug Discovery. 1. Background and Peptide Combinatorial Libraries", *Journal of Medicinal Chemistry*, vol. 37, No. 9, pp. 1233–1251, (Apr. 29, 1994).

Ghose, A. K. and Gordon M. Crippen, "Use of Physicochemical Parameters in Distance Geometry and Related Three–Dimensional Qantitative Structure–Activity Relationships: A Demonstration Using *Escherichia coli* Dihydrofolate Reductase Inhibitors", *Journal of Medicinal Chemistry*, vol. 28, No. 3, pp. 333–346, (1985). (No Month).

Good, A. C. et al., "Structure–Activity Relationships from Molecular Similarity Matrices", *Journal of Medicinal Chemistry*, vol. 36, No. 4, pp. 433–438, (Feb. 19, 1993).

Gordon, E. M., "Applications of Combinatorial Technologies to Drug Discovery. 2. Combinatorial Organic Synthesis, Library Screening Strategies, and Future Directions", *Journal of Medicinal Chemistry*, vol. 37, No. 10, (May 13, 1994).

Hartigan, J. A., "Representation of Similarity Matrices By Trees", *Journal of the American Statistical Association*, vol. 62, No. 320, pp. 1140–1158, (Dec., 1967).

Hopfinger, A. J., "A QSAR Investigation of Dihydrofolate Reductase Inhibition by Baker Triazines based upon Molecular Shape Analysis", *Journal of the American Chemical Society*, vol. 102, No. 24, pp. 7196–7206, (Nov. 19, 1980).

Jackson, R. C., "Update on computer–aided drug design", *Current Opinion in Biotechnology*, vol. 6, No. 6, pp. 646–651, (Dec., 1995).

Kim, K. H., "Comparative molecular field analysis (CoFMA)", *Molecular Similarity in Drug Design*, ed. P. M. Dean, Blackie Academic & Professional, 1995, Ch. 12 (pp. 291–324).

Kohonen, T., "Self–Organized Formation of Topologically Correct Feature Maps", *Biological Cybernetics*, vol. 43, pp. 59–69, (1982). (No Month).

Koile, K. and Richard Shapiro, "Building A Collaborative Drug Design System", *Proceedings of the 25h Hawaii International Conference on System Sciences*, pp. 706–716, (1992). (No Month).

Kowalski, B. R. and C. F. Bender, "Pattern Recognition. II. Linear and Nonlinear Methods for Displaying Chemical Data", *Journal of the American Chemical Society*, pp. 686–693, (Feb. 7, 1973).

Kruskal, J. B., "Nonmetric Multidimensional Scaling: A Numerical Method", *Psychometrika*, vol. 29, No. 2, pp. 115–129, (Jun., 1964).

Lengauer, T. and Matthias Rarey, "Computational methods for biomolecular docking", *Current Opinion in Structural Biology*, vol. 6, No. 3, pp. 402–406, (Jun., 1996).

Luke, B. T., "Evolutionary Programming Applied to the Development of Quantitative Structure–Activity Relationships and Quantitative Structure–Property Relationships", *Journal of Chemical Information and Computer Sciences*, vol. 34, pp. 1279–1287, (Nov./Dec., 1994).

Martin, E. J. et al., "Does Combinatorial Chemistry Obviate Computer–Aided Drug Design?", *Reviews in Computational Chemistry*, vol. 10, pp. 75–99, (1997). (No Month).

Martin, E. J. et al., "Measuring Diversity: Experimental Design of Combinatorial Libraries for Drug Discovery", *Journal of Medicinal Chemistry*, vol. 38, No. 9, pp. 1431–1436, (Apr. 28, 1995).

McMartin, C. and Regine S. Bohacek, "QXP: Powerful, rapid computer algorithms for structure–based drug design", *Journal of Computer–Aided Molecular Design*, vol. 11, pp. 333–344, (1997). (No Month).

Mezey, P. G. and P. Duane Walker, "Fuzzy molecular fragments in drug research", *Drug Discovery Today*, vol. 2, No. 4, (Apr., 1997), pp. 132–137.

Müller, K., "On the paradigm shift from rational to random design", *Journal of Molecular Structure (Theochem)*398–399, Special Issue, pp. 467–471, (1997). (No Month).

Myers, P., "The Design Of A Universal, Informer™ Library", Combichem, Inc., Date unknown, 11 pages.

Oinuma, H. et al., "Neural Networks Applied to Structure-Activity Relationships", *Journal of Medicinal Chemistry*, vol. 33, No. 3, pp. 905–908, (1990). (No Month).

Omohundro, S. M., "Bumptrees for Efficient Function, Constraint, and Classification Learning", International Computer Science Institute, pp. 693–699, Date unknown.

Parrill, A. L., "Evolutionary and genetic methods in drug design", *Drug Discovery Today*, vol. 1, No. 12, pp. 514–521, (Dec., 1996).

Polanski, J., "A neural network for the simulation of biological systems", *Journal of Molecular Structure (Theochem)*398–399, Special Issue, pp. 565–571, (1997). (No Month).

Ramos–Nino, M. E. et al., "A comparison of quantitative structure–activity relationships for the effect of benzoic and cinnamic acids on Listeria monocytogenes using multiple linear regression, artificial neural network and fuzzy systems", *Journal of Applied Microbiology*, vol. 82, No. 2, pp. 168–175, (Feb., 1997).

Rogers, D. and A. J. Hopfinger, "Application of Genetic Function Approximation to Quantitative Structure–Activity Relationships and Quantitative Structure–Property Relationships", *Journal of Chemical Information and Computer Sciences*, vol. 34, No. 4, pp. 854–866, (Jul./Aug., 1994).

Sammon, J. W., Jr., "A Nonlinear Mapping for Data Structure Analysis", *IEEE Transactions on Computers*, vol. C–18, No. 5, pp. 401–409, (May, 1969).

Simon, Z. et al., "Mapping of Dihydrofolate–reductase Receptor Site by Correlation with Minimal Topological (Steric) Differences", *Journal of Theoretical Biology*, vol. 66, No. 3, pp. 485–495, (Jun. 7, 1997).

Smellie, A. S. et al., "Fast Drug–Receptor Mapping by Site–Directed Distances: A Novel Method of Predicting New Pharmacological Leads", *Journal of Chemical Information and Computer Sciences*, vol. 31, No. 3, pp. 386–392, (Aug., 1991).

Specht, D. F., "A General Regression Neural Network", *IEEE Transactions on Neural Networks*, vol. 2, No. 6, pp. 568–576, (Nov., 1991).

Svozil, D. et al., "Neural Network Prediction of the Solvatochromic Polarity/Polarizability Parameter $II^{H_2}$", *Journal of Chemical Information and Computer Sciences*, vol. 37, No. 2, (1997). (No Month).

Todorov, N. P. and P. M. Dean, "Evaluation of a method for controlling molecular scaffold diversity in de novo ligand design", *Journal of Computer–Aided Molecular Design*, vol. 11, pp. 175–192, (1997). (No Month).

Torgerson, W. S., "Multidimensional Scaling: I. Theory and Method", *Psychometrika*, vol. 17, No. 4, pp. 401–419, (Dec., 1952).

Vapnik, V., "Principles of Risk Minimization for Learning Theory", *Advances in Neural Information Processing Systems 4*, pp. 831–838, Date unknown.

Vapnik, V. and L. Bottou, "Local Algorithms for Pattern Recognition and Dependencies Estimation", *Neural Computation*, vol. 5, No. 6, pp. 893–909, (Nov., 1993).

Viswanadhan, V. N. et al., "Mapping the binding site of the nucleoside transporter protein: a 3D–QSAR study", *Biochimica et Biophysica Acta*, vol. 1039, No. 3, pp. 356–366, (1990). (No Month).

Warr, W. A., "Exploiting Molecular Diversity: Small Molecule Libraries for Drug Discovery", Report of Conference held in La Jolla, California, Jan. 23–25, 1995. (No Month).

Westhead, D. R. et al., "A comparison of heuristic search algorithms for molecular docking", *Journal of Computer–Aided Molecular Design*, vol. 11, pp. 209–228, (1997). (No Month).

Willett, P., "Genetic algorithms in molecular recognition and design", *Trends in Biotechnology*, vol. 13, No. 12, pp. 516–521, (Dec., 1995).

Willett, P. and Vivienne Winterman, "A Comparison of Some Measures for the Determination of Inter–Molecular Structural Similarity Measures of Inter–Molecular Structural Similarity", *Quantitative Structure–Activity Relationships,* vol. 5, No. 1, pp. 18–25, (Mar., 1986).

Zadeh, L. A., "Communication Fuzzy Algorithms", *Information and Control,* vol. 12, No. 2, pp. 94–102, (Feb., 1968).

Zadeh, L. A., "Fuzzy Sets", *Information and Control,* vol. 8, No. 3, pp. 338–353, (Jun., 1965).

Domine, D. et al., "Non–Linear Mapping for Structure–Activity and Structure–Property Modelling," Journal of Chemometrics, John Wiley & Sons, Ltd., vol. 7, No. 4, Jul.–Aug. 1993, pp. 227–242.

* cited by examiner

SYSTEM, METHOD, AND COMPUTER PROGRAM PRODUCT FOR REPRESENTING PROXIMITY DATA IN A MULTI-DIMENSIONAL SPACE

CROSS-REFERENCE TO RELATED APPLICATIONS

This application is a continuation-in-part of U.S. patent application Ser. No.08/963,872, filed Nov. 4, 1997, now U.S. Pat. No. 6,295,514, which claims the benefit of U.S. Provisional Patent Application Ser. No. 60/030,187, filed Nov. 4, 1996.

The above referenced applications are incorporated herein by reference in their entireties.

BACKGROUND OF THE INVENTION

1. Field of the Invention

The present invention is directed to data analysis and, more particularly, to representation of proximity data in multi-dimensional space.

2. Related Art

Multidimensional scaling (MDS) and non-linear mapping (NLM) are techniques for generating display maps, including non-linear maps, of objects wherein the distances between the objects represent relationships between the objects.

MDS and NLM were introduced by Torgerson, *Phychometrika*, 17:401 (1952); Kruskal, *Psychometrika*, 29:115 (1964); and Sammon, *IEEE Trans. Comput.*, C-18:401 (1969) as a means to generate low-dimensional representations of psychological data. Multidimensional scaling and non-linear mapping are reviewed in Schiffman, Reynolds and Young, *Introduction to Multidimensional Scaling*, Academic Press, New York (1981); Young and Hamer, *Multidimensional Scaling: History, Theory and Applications*, Erlbaum Associates, Inc., Hillsdale, N.J. (1987); and Cox and Cox, Multidimensional Scaling, Number 59 in *Monographs in Statistics and Applied Probability*, Chapman-Hall (1994). The contents of these publications are incorporated herein by reference in their entireties.

MDS and NLM (these are generally the same, and are hereafter collectively referred to as MDS) represent a collection of methods for visualizing proximity relations of objects by distances of points in a low-dimensional Euclidean space. Proximity measures are reviewed in Hartigan, *J. Am. Statist. Ass.*, 62:1140 (1967), which is incorporated herein by reference in its entirety.

In particular, given a finite set of vectorial or other samples $A=\{a_i, i=1, \ldots, k\}$, a relationship function $r_{ij}=r(a_i, a_j)$, with $a_i, a_j \in A$, which measures the similarity or dissimilarity between the i-th and j-th objects in A, and a set of images $X=\{x_i, \ldots, x_k; x_i \in R^m\}$ of A on an m-dimensional display plane ($R^m$ being the space of all m-dimensional vectors of real numbers), the objective is to place $x_i$ onto the display plane in such a way that their Euclidean distances $d_{ij}=\|x_i-x_j\|$ approximate as closely as possible the corresponding values $r_{ij}$. This projection, which in many cases can only be made approximately, is carried out in an iterative fashion by minimizing an error function which measures the difference between the original, $r_{ij}$, and projected, $d_{ij}$, distance matrices of the original and projected vector sets.

Several such error functions have been proposed, most of which are of the least-squares type, including Kruskal's 'stress':

$$S = \sqrt{\frac{\sum_{i<j}^{k}(r_{ij}-d_{ij})^2}{\sum_{i<j}^{k} r_{ij}^2}} \qquad \text{EQ. 1}$$

Sammon's error criterion:

$$E = \frac{\sum_{i<j}^{k}\frac{(r_{ij}-d_{ij})^2}{r_{ij}}}{\sum_{i<j}^{k} r_{ij}} \qquad \text{EQ. 2}$$

and Lingoes' alienation coefficient:

$$K = \sqrt{\frac{\sum_{i<j}^{k}(r_{ij}d_{ij})^2}{\sum_{i<j}^{k} d_{ij}}} \qquad \text{EQ. 3}$$

where $d_{ij}=\|x_i-x_j\|$ is the Euclidean distance between the images $x_i$ and $x_j$ on the display plane.

Generally, the solution is found in an iterative fashion by:

(1) computing or retrieving from a database the relationships $r_{ij}$;

(2) initializing the images $x_i$;

(3) computing the distances of the images $d_{ij}$ and the value of the error function (e.g. S, E or K in EQ. 1–3 above);

(4) computing a new configuration of the images $x_i$ using a gradient descent procedure, such as Kruskal's linear regression or Guttman's rank-image permutation; and (5) repeating steps 3 and 4 until the error is minimized within some prescribed tolerance.

For example, the Sammon algorithm minimizes EQ. 2 by iteratively updating the coordinates $x_i$ using Eq 4:

$$x_{pq}(m+1)=x_{pq}(m)-\lambda\Delta_{pq}(m) \qquad \text{EQ. 4}$$

where m is the iteration number, $x_{pq}$ is the q-th coordinate of the p-th image $x_p$, $\lambda$ is the learning rate, and $$\Delta_{pq}(m) = \frac{\frac{\partial E(m)}{\partial x_{pq}(m)}}{\left|\frac{\partial^2 E(m)}{\partial x_{pq}(m)^2}\right|} \qquad \text{EQ. 5}$$

The partial derivatives in EQ. 5 are given by:

$$\frac{\partial E(m)}{\partial x_{pq}(m)} = -2\frac{\sum_{j=1,j\neq p}^{k}\frac{r_{pj}-d_{pj}}{r_{pj}d_{pj}}(x_{pq}-x_{jq})}{\sum_{i<j}^{k} r_{ij}} \qquad \text{EQ. 6}$$

-continued $$\frac{\partial^2 E(m)}{\partial x_{pq}(m)^2} = \text{EQ. 7}$$

$$-2 \frac{\sum_{i<j}^{k} \frac{1}{r_{pj}d_{pj}} \left[ (r_{pj} - d_{pj}) - \frac{(x_{pq} - x_{jq})^2}{d_{pj}} \left( 1 + \frac{(r_{pj} - d_{pj})}{d_{pj}} \right) \right]}{\sum_{i<j}^{k} r_{ij}}$$

The mapping is obtained by repeated evaluation of EQ. 2, followed by modification of the coordinates using EQ. 4 and 5, until the error is minimized within a prescribed tolerance.

The general refinement paradigm above is suitable for relatively small data sets but has one important limitation that renders it impractical for large data sets. This limitation stems from the fact that the computational effort required to compute the gradients (i.e., step (4) above), scales to the square of the size of the data set. For relatively large data sets, this quadratic time complexity makes even a partial refinement intractable.

What is needed is a system, method and computer program product for representing proximity data in a multi-dimensional space, that scales favorably with the number of objects and that can be applied to both small and large data sets. Moreover, what is needed is a system, method and computer program product that can be effective with missing data and/or data containing bounded or unbounded uncertainties, noise or errors.

SUMMARY OF THE INVENTION

The present invention is a system, method and computer program product for representing precise or imprecise measurements of similarity/dissimilarity (relationships) between objects preferably as distances between points in a multi-dimensional space that represent the objects. The algorithm uses self-organizing principles to iteratively refine an initial (random or partially ordered) configuration of points using stochastic relationship/distance errors. The data can be complete or incomplete (i.e. some relationships between objects may not be known), exact or inexact (i.e. some or all relationships may be given in terms of allowed ranges or limits), symmetric or asymmetric (i.e. the relationship of object A to object B may not be the same as the relationship of B to A) and may contain systematic or stochastic errors.

The relationships between objects may be derived directly from observation, measurement, a priori knowledge, or intuition, or may be determined directly or indirectly using any suitable technique for deriving proximity (relationship) data.

The present invention iteratively analyzes sub-sets of objects in order to represent them in a multi-dimensional space that represents relationships between the objects.

In an exemplary embodiment, the present invention iteratively analyzes sub-sets of objects using conventional multi-dimensional scaling or non-linear mapping algorithms.

In another exemplary embodiment, relationships are defined as pair-wise relationships or pair-wise similarities/dissimilarities between pairs of objects and the present invention iteratively analyzes a pair of objects at a time. Preferably, sub-sets are evaluated pair-wise, as a double-nested loop.

In the following discussion, the terms relationship, similarity or dissimilarity is used to denote a relationship between a pair of objects. The term display map is used to denote a collection of images on an n-dimensional space that represents the original objects. The term distance is used to denote a distance between images on a display map that correspond to the objects.

Examples of the present invention are provided herein, including examples of the present invention implemented with chemical compound data and relationships. It is to be understood, however, that the present invention is not limited to the examples presented herein. The present invention can be implemented in a variety of applications.

For example, while the specific embodiment described herein utilizes distances between points to represent similarity/dissimilarity between objects, the invention is intended and adapted to utilize any display attribute to represent similarity/dissimilarity between objects, including but not limited to font, size, color, grey scale, italics, underlining, bold, outlining, border, etc. For example, the similarity/dissimilarity between two objects may be represented by the relative sizes of points that represent the objects.

Further features and advantages of the present invention, as well as the structure and operation of various embodiments of the present invention, are described in detail below with reference to the accompanying drawings.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

The present invention will be described with reference to the accompanying drawings, wherein.

In the drawings, like reference numbers indicate identical or functionally similar elements. Also, the leftmost digit(s) of the reference numbers identify the drawings in which the associated elements are first introduced.

DETAILED DESCRIPTION OF THE PREFERRED EMBODIMENTS

Table of Contents

Figure 1:
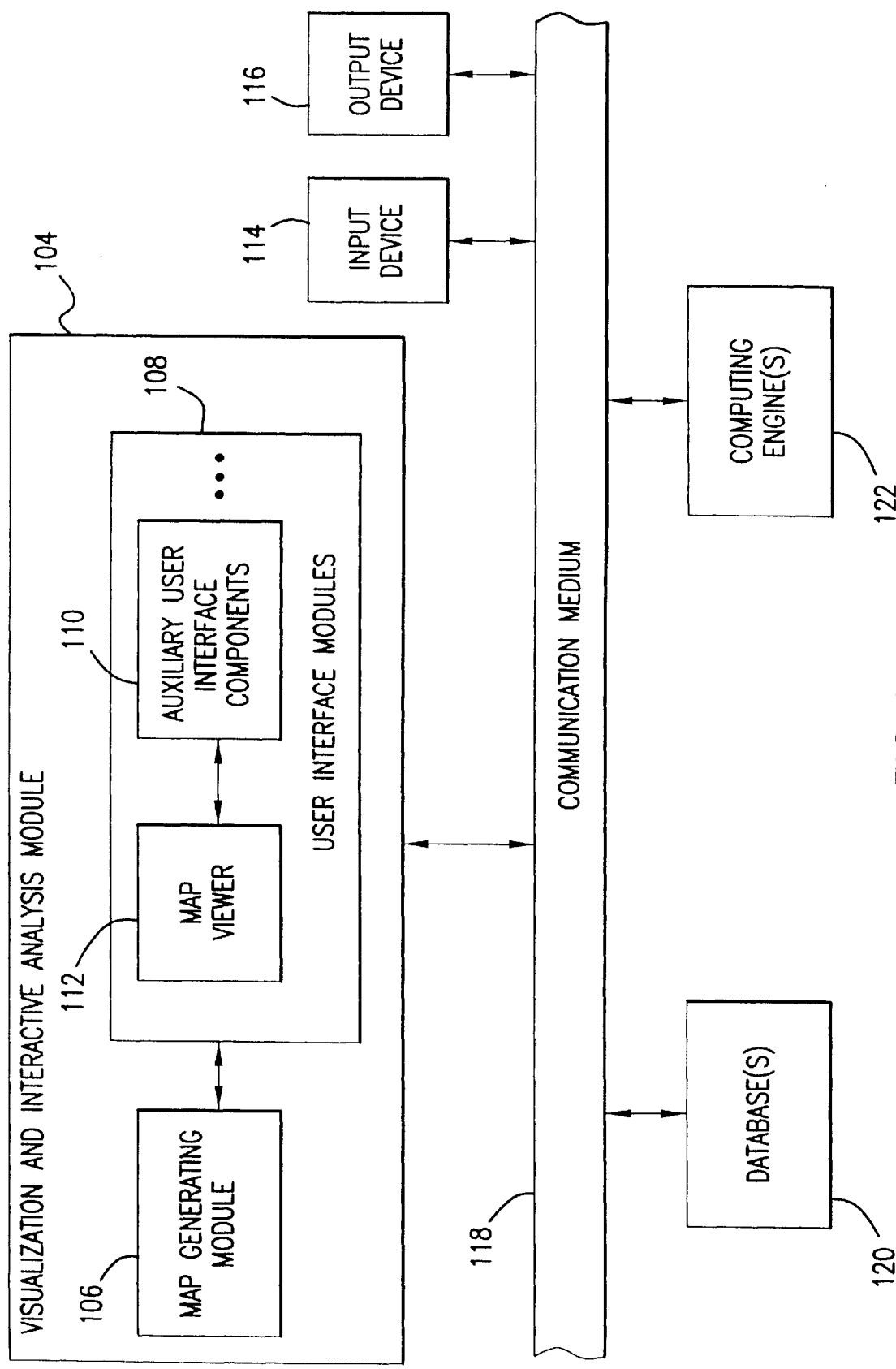
FIG. 1 illustrates a block diagram of a computing environment according to an embodiment of the invention.

I. Overview of the Present Invention
II. Sub-Set Selection
III. Complete Pair-Wise Relationship Matrices without Uncertainties
IV. Sparse Pair-Wise Relationship Matrices without Uncertainties V. Pair-Wise Relationship Matrices with Bounded Uncertainties
VI. Pair-Wise Relationship Matrices with Unbounded Uncertainties (Corrupt Data)
VII. Modifications of the Basic Algorithm
VIII. Evaluation Properties (Features), Relationships and Distance Measures
   A. Evaluation Properties Having Continuous or Discrete Real Values
      1. Relationships or Distance Measures Where Values of Evaluation Properties Are Continuous or Discrete Real Numbers
   B. Evaluation Properties Having Binary Values
      1. Distance Measures Where Values of Evaluation Properties Are Binary
   C. Scaling of Evaluation Properties
IX. Implementation of the Invention
   A. Generally
   B. Implementation of the Invention in a Computer Program Product
   C. Operation of the Present Invention
X. Example of the Invention
   A. Operation of the Exemplary Embodiment
XI. Conclusions I. Overview of the Present Invention The present invention is a system, method and computer program product for representing precise or imprecise measurements of similarity/dissimilarity (relationships) between objects as distances between points (or using other display attributes or techniques) in a multi-dimensional space that represent the objects. The algorithm uses self-organizing principles to iteratively refine an initial (random or partially ordered) configuration of points using stochastic relationship/distance errors. The data can be complete or incomplete (i.e. some relationships between objects may not be known), exact or inexact (i.e. some or all relationships may be given in terms of allowed ranges or limits), symmetric or asymmetric (i.e. the relationship of object A to object B may not be the same as the relationship of B to A) and may contain systematic or stochastic errors.

The relationships between objects may be derived directly from observation, measurement, a priori knowledge, or intuition, or may be determined directly or indirectly using any suitable technique for deriving proximity (relationship) data.

The present invention iteratively analyzes sub-sets of objects in order to represent them in a multi-dimensional space that represent the objects.

In an exemplary embodiment, the present invention iteratively analyzes sub-sets of objects using conventional multi-dimensional scaling or non-linear mapping algorithms.

In another exemplary embodiment, relationships are defined as pair-wise relationships or pair-wise similarities/dissimilarities between pairs of objects and the present invention iteratively analyzes a pair of objects at a time. Preferably, sub-sets are evaluated pair-wise, as a double-nested loop.

In an alternate embodiment, relationships are defined as N-wise relationships or N-wise similarities/dissimilarities between multiple objects, and the present invention iteratively analyzes multiple objects at a time, where N is preferably greater than 1. Implementation of this alternate embodiment will be apparent to persons skilled in the relevant art(s).

The term "object" refers to any entity, data, property, attribute, component, element, ingredient, item, etc., where it would be useful to represent the similarity/dissimilarity between instances of or different ones of any such entity, data, property, attribute, component, element, ingredient, item, etc. Without limitation but by way of illustration only, objects include, for example, chemical compounds, processes, machines, compositions of matter, articles of manufacture, electrical devices, mechanical devices, financial data, financial instruments, financial trends, financial related traits and characteristics, software products, human traits and characteristics, scientific properties, traits, and characteristics, etc. In an embodiment, the invention operates with any entity, data, property, attribute, component, element, ingredient, item, etc., except chemical compounds.

II. Sub-Set Selection

The present invention iteratively analyzes sub-sets of objects in order represent them in a multi-dimensional space that represent the relationships between the objects. In an exemplary embodiment, the present invention iteratively analyzes sub-sets of objects using conventional multi-dimensional scaling or non-linear mapping algorithms. In this embodiment, the objects in a selected sub-set are analyzed as a group using a conventional algorithm, such as, but not limited to, those described above, for example. In particular, the coordinates of the images corresponding to the objects comprising that sub-set are refined using convention multi-dimensional scaling, non-linear mapping or any other suitable algorithm, or the pair-wise refinement algorithm described below.

In this embodiment, sub-sets of objects can be selected randomly, semi-randomly, systematically, partially systematically, etc. As sub-sets of objects are analyzed and their distances are revised, the set of objects tends to self-organize. In this way, large data sets can be accommodated with conventional multi-dimensional scaling or non-linear mapping algorithms.

In another exemplary embodiment, relationships are defined as pair-wise relationships or pair-wise similarities/dissimilarities between pairs of objects and the present invention iteratively analyzes a pair of objects at a time. Pairs of objects can be selected randomly, semi-randomly, systematically, partially systematically, etc. Novel algorithms and techniques for pair-wise analysis is provided in the sections below. This embodiment is described for illustrative purposes only and is not limiting.

In an alternate embodiment, relationships are defined as N-wise relationships or N-wise similarities/dissimilarities between multiple objects, and the present invention iteratively analyzes multiple objects at a time, where N is preferably greater than 1. Implementation of this alternate embodiment will be apparent to persons skilled in the relevant art(s).

III Complete Pair-Wise Relationship Matrices without Uncertainties

A preferred approach adopted herein is to use iterative refinement based on stochastic or instantaneous errors. The discussion in this section assumes that all pair-wise relationships are known, and they are all exact. As in traditional MDS, the method starts with an initial configuration of points generated at random or by some other procedure (vide infra). This initial configuration is then continuously refined by repeatedly selecting two points i, j, at random, and modifying their coordinates on the display map according to EQ. 8:

$$x_i(t+1) = f(t, x_i(t), x_j(t), r_{ij}) \quad \text{EQ. 8}$$

where t is the current iteration, $x_i(t)$ and $x_j(t)$ are the current coordinates of the i-th and j-th points on the display map, $x_i(t+1)$ are the new coordinates of the i-th point on the display map, and $r_{ij}$ is the pair-wise relationship between the i-th and j-th objects that we attempt to approximate on the display map (vide supra). $f(.)$ in EQ. 8 above can assume any functional form. Ideally, this function should try to minimize the difference between the actual and target distance between the i-th and j-th points. For example, $f(.)$ may be given by EQ. 9:

$$x_i(t+1) = \quad \text{EQ. 9}$$
$$f(t, x_i(t), x_j(t), r_{ij}) = x_i(t) + 0.5\lambda(t)\frac{(r_{ij} - d_{ij}(t))}{d_{ij}(t)}(x_i(t) - x_j(t))$$

where t is the iteration number, $d_{ij}=\|x_i(t)-x_j(t)\|$, and $\lambda(t)$ is an adjustable parameter, referred to hereafter as the 'learning rate', borrowing from neural network terminology. This process is repeated for a fixed number of cycles, or until some global error criterion is minimized within some prescribed tolerance. A large number of iterations are typically required to achieve statistical accuracy.

The method described above is reminiscent of neural network back-propagation training (Werbos, *Beyond Regression: New Tools for Prediction and Analysis in the Behavioral Sciences*. PhD Thesis, Harvard University, Cambridge, Mass. (1974), and Rumelhart and McClelland, Eds., *Parallel Distributed Processing: Explorations in the Microstructure of Cognition*. Vol. 1, MIT Press, Cambridge, Mass. (1986)) and Kohonen's self-organizing principle (Kohonen, *Biological Cybernetics*, 43:59 (1982)).

The learning rate $\lambda(t)$ in EQ. 9 plays a key role in ensuring convergence. If $\lambda$ is too small, the coordinate updates are small, and convergence is slow. If, on the other hand, $\lambda$ is too large, the rate of learning may be accelerated, but the display map may become unstable (i.e. oscillatory). Typically, $\lambda$ ranges in the interval [0, 1] and may be fixed, or it may decrease monotonically during the refinement process. Moreover, $\lambda$ may also be a function of i, j and/or $r_{ij}$ and can be used to apply different weights to certain objects and/or relationships. For example, $\lambda$ may be computed by:

$$\lambda(t) = \left(\lambda_{\min} + t\lambda_{\max} - \frac{\lambda_{\min}}{T}\right)\frac{1}{1+ar_{ij}} \quad \text{EQ. 10}$$

or $$\lambda(t) = \left(\lambda_{\min} + t\lambda_{\max} - \frac{\lambda_{\min}}{T}\right)e^{-ar_{ij}} \quad \text{EQ. 11}$$

where $\lambda_{max}$ and $\lambda_{min}$ are the (unweighted) starting and ending learning rates such that $\lambda_{max}, \lambda_{min} \in [0,1]$, t is the total number of refinement steps (iterations), t is the current iteration number, and $\alpha$ is a constant scaling factor. EQS. 10 and 11 have the effect of decreasing the correction at large separations, thus creating a display map which preserves short-range interactions more faithfully than long-range ones. Weighting is discussed in greater detail below.

One of the main advantages of this approach is that it makes partial refinements possible. It is often sufficient that the pair-wise relationships are represented only approximately to reveal the general structure and topology of the data. Unlike traditional MDS, this approach allows very fine control of the refinement process. Moreover, as the display map self-organizes, the pair-wise refinements become cooperative, which partially alleviates the quadratic nature of the problem.

The embedding procedure described above does not guarantee convergence to the global minimum (i.e. the most faithful embedding in a least-squares sense). If so desired, the refinement process may be repeated a number of times from different starting configurations and/or random number seeds. Generally, the absolute coordinates in the display map carry no physical significance. What is important are the relative distances between points, and the general structure and topology of the data (presence, density and separation of clusters, etc.).

The method described above is ideally suited for both metric and non-metric scaling. The latter is particularly useful when the pair-wise relationships do not obey the distance postulates and, in particular, the triangle inequality. Although an 'exact' projection is only possible when the pair-wise relationship matrix is positive definite, meaningful maps can still be obtained even when this criterion is not satisfied. As mentioned above, the overall quality of the projection is determined by a sum-of-squares error function such as those shown in EQ. 1–3.

The general algorithm described above can also be applied when the pair-wise relationship matrix is incomplete, i.e. when some of the pair-wise relationships are unknown, when some of the pair-wise relationships are uncertain or corrupt, or both of the above. These cases are discussed separately below.

IV. Sparse Pair-Wise Relationship Matrices without Uncertainties

The general algorithm described above can also be applied when the pair-wise relationship matrix is incomplete, i.e. when some of the pair-wise relationships are unknown. In this case, a similar algorithm to the one described above can be used, with the exception that the algorithm iterates over pairs of points for which the relationships are known. In this case, the algorithm identifies configurations in space that satisfy the known pair-wise relationships; the unknown pair-wise relationships adapt during the course of refinement and eventually assume values that lead to a satisfactory embedding of the known relationships.

Depending on the number of missing data, there may be more than one satisfactory embeddings (mappings) of the original relationship matrix. In this case, different configurations (maps) may be derived from different starting configurations or random number seeds. In some applications such as searching the conformational space of molecules, this feature provides a significant advantage over some alternative techniques. All variants of the original algorithm (see Sections below) can be used in this context.

V. Pair-Wise Relationship Matrices with Bounded Uncertainties

The general algorithm described above can also be applied when the pair-wise relationships contain bounded uncertainties, i.e. when some of the pair-wise relationships are only known to within certain fixed tolerances (for example, the relationships are known to lie within a range or set of ranges with prescribed upper and lower bounds). In this case, a similar algorithm to the one described above can be used, with the exception that the distances on the display map are corrected only when the corresponding points lie outside the prescribed bounds. For example, assume that the relationship between two objects, i and j, is given in terms of an upper and lower bound, $r_{max}$ and $r_{min}$, respectively. When this pair of objects is selected during the course of the refinement, the distance of the corresponding images on the display map is computed, and denoted as $d_{ij}$. If $d_{ij}$ is larger than $r_{max}$, the coordinates of the images are updated using $r_{max}$ as the target distance (Eq. 12):

$$x_i(t+1)=f(t, x_i(t), x_j(t), r_{max}) \qquad \text{EQ. 12}$$

Conversely, if $d_{ij}$ is smaller than $r_{min}$, the coordinates of the images are updated using $r_{min}$ as the target distance (Eq. 13):

$$x_i(t+1)=f(t, x_i(t), x_j(t), r_{min}) \qquad \text{EQ. 13}$$

If $d_{ij}$ lies between the upper and lower bounds (i.e. if $r_{min} \leq d_{ij} \leq r_{max}$), no correction is made. In other words, the algorithm attempts to match the upper bound if the current distance between the images is greater than the upper bound, or the lower bound if the current distance between the images is lower than the lower bound. If the distance between the images lies within the upper and lower bounds, no correction is made.

This algorithm can be extended in the case where some of the pair-wise relationships are given by a finite set of allowed discrete values, or by a set of ranges of values, or some combination thereof. For the purposes of the discussion below, we consider discrete values as ranges of zero width (e.g. the discrete value of 2 can be represented as the range [2,2]).

Figure 5:
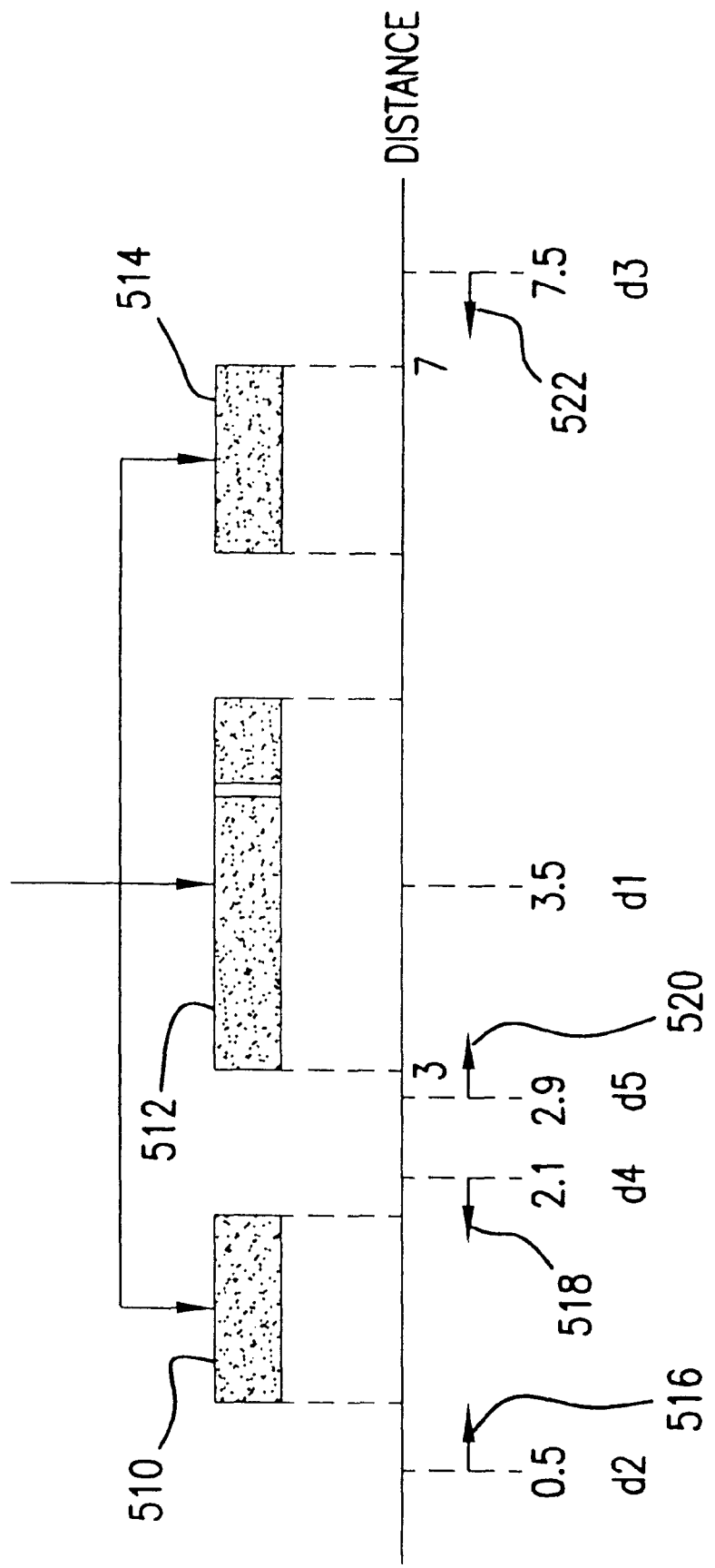
FIG. 5 conceptually illustrates relationships between objects, wherein the relationships are known within certain tolerances.

Various possibilities for a single hypothetical pair-wise relationship and the current distance of the corresponding images on the display map are illustrated in FIG. 5, where shaded areas 510, 512 and 514 denote allowed ranges for a given pair-wise relationship. Distances d1–d5 illustrate 5 different possibilities for the current distance between the corresponding images on the display map. Arrows 516, 518, 520 and 522 indicate the direction of the correction that should be applied on the images on the map. Arrows 518 and 522 point to the left, indicating that the coordinates of the associated images on the display map should be updated so that the images come closer together. Arrows 516 and 520 point to the right, indicating that the coordinates of the associated images should be updated so that the images become more distant.

As in the case of a single range, if the current distance of a selected pair of images on the display map lies within any of the prescribed ranges, no coordinate update takes place (i.e., case d1 in FIG. 5). If not, the correction is applied using the nearest range boundary as the target distance (i.e., cases d2–d5 in FIG. 5). For example, if the relationship between a given pair of objects lies in the ranges [1,2], [3,5] and [6,7] and the current distance of the respective images is 2.9 (d5 in FIG. 5), the correction takes place using 3 as the target distance ($r_{ij}$) in Eq. 8. If, however, the current distance is 2.1, the coordinates are updated using 2 as the target distance ($r_{ij}$) in Eq. 8.

This deterministic criterion may be replaced by a stochastic or probabilistic one in which the target distance is selected either randomly or with a probability that depends on the difference between the current distance and the two nearest range boundaries. In the example described above (d5 in FIG. 5), a probabilistic choice between 2 and 3 as a target distance could be made, with probabilities of, for example, 0.1 and 0.9, respectively (that is, 2 could be selected as the target distance with probability 0.1, and 3 with probability 0.9). Any method for deriving such probabilities can be used. Alternatively, either 2 or 3 could be chosen as the target distance at random.

For example, bounded uncertainties in the pair-wise relationships may represent stochastic or systematic errors or noise associated with a physical measurement, and can, in general, differ from one pair-wise relationship to another. A typical example are the Nuclear Overhauser Effects (NOE's) in multi-dimensional Nuclear Magnetic Resonance spectrometry.

An alternative algorithm for dealing with uncertainties is to reduce the magnitude of the correction for pairs of objects whose relationship is thought to be uncertain. In this scheme, the magnitude of the correction, as determined by the learning rate in Eq. 9, for example, is reduced for pair-wise relationships which are thought to be uncertain. The magnitude of the correction may depend on the degree of uncertainty associated with the corresponding pair-wise relationship (for example, the magnitude of the correction may be inversely proportional to the uncertainty associated with the corresponding pair-wise relationship). If the existence and/or magnitude of the errors is unknown, then the errors can be determined automatically by the algorithm. (see Section V below).

VI. Pair-Wise Relationship Matrices with Unbounded Uncertainties (Corrupt Data)

The ideas described in the preceding Sections can be applied when some of the pair-wise relationships are thought to contain corrupt data, that is when some of the pair-wise relationships are incorrect and bear essentially no relationship to the actual values. In this case, 'problematic' relationships can be detected during the course of the algorithm, and removed from subsequent processing. In other words, the objective is to identify the corrupt entries and remove them from the relationship matrix. This process results in a sparse relationship matrix, which can be refined using the algorithm in Section 1.2 above.

VII. Modifications of the Basic Algorithm

In many cases, the algorithm described above may be accelerated by pre-ordering the data using a suitable statistical method. For example, if the proximities are derived from data that is available in vectorial or binary form, the initial configuration of the points on the display map may be computed using Principal Component Analysis. In a preferred embodiment, the initial configuration may be constructed from the first 3 principal components of the feature matrix (i.e. the 3 latent variables which account for most of the variance in the data). In practice, this technique can have profound effects in the speed of refinement. Indeed, if a random initial configuration is used, a significant portion of the training time is spent establishing the general structure and topology of the display map, which is typically characterized by large rearrangements. If, on the other hand, the input configuration is partially ordered, the error criterion can be reduced relatively rapidly to an acceptable level.

If the data is highly clustered, by virtue of the sampling process low-density areas may be refined less effectively than high-density areas. In an exemplary embodiment, this tendency may be partially compensated by a modification to the original algorithm which increases the sampling probability in low-density areas. In one embodiment, the center of mass of the display map is identified, and concentric shells centered at that point are constructed. A series of regular refinement iterations are then carried out, each time selecting points from within or between these shells. This process is repeated for a prescribed number of cycles. This phase is then followed by a phase of regular refinement using global sampling, and the process is repeated.

Generally, the basic algorithm does not distinguish short-range distances from long-range distances. EQ. 10 and 11 describe a method to ensure that short-range distances are preserved more faithfully than long-range distances through the use of weighting.

An alternative (and complementary) approach is to ensure that points at close separation are sampled more extensively than points at long separation. For example, an alternating sequence of global and local refinement cycles, similar to the one described above, can be employed. In this embodiment, a phase of global refinement is initially carried out, after which, the resulting display map is partitioned into a regular grid. The points (objects) in each cell of the grid are then subjected to a phase of local refinement (i.e. only points from within the same cell are compared and refined). Preferably, the number of sampling steps in each cell should be proportional to the number of points contained in that cell. This process is highly parallelizable. This local refinement phase is then followed by another global refinement phase, and the process is repeated for a prescribed number of cycles, or until the embedding error is minimized within a prescribed tolerance. Alternatively, the grid method may be replaced by another suitable method for identifying proximal points, such as a k-d tree, for example.

The methods described herein may be used for incremental refinement. That is, starting from an organized display map of a set of point, a new set of points may be added without modification of the original map. Strictly speaking, this is statistically acceptable if the new set of points is significantly smaller than the original set. In an exemplary embodiment, the new set of points may be 'diffused' into the existing map, using a modification of the basic algorithm described above. In particular, EQ. 8 and 9 can be used to update only the incoming points. In addition, the sampling procedure ensures that the selected pairs contain at least one point from the incoming set. That is, two points are selected at random so that at least one of these points belongs to the incoming set. Alternatively, each new point may be diffused independently using the approach described above.

VIII. Evaluation Properties (Features), Relationships and Distance Measures

In an exemplary embodiment, relationships between objects may be represented as similarities/dissimilarities between the objects on a display map and may be derived from properties or features associated with the objects. Any similarity measure can be used to construct the display map. The properties or features that are being used to evaluate similarity or dissimilarity are sometimes herein collectively called "evaluation properties."

For example, if the objects are chemical compounds, similarity between objects can be based on structural similarity, chemical similarity, physical similarity, biological similarity, and/or some other type of similarity measure which can be derived from the structure or identity of the compounds.

A. Evaluation Properties Having Continuous or Discrete Real Values

Similarity measures may be derived from a list of evaluation properties associated with a set of objects. For example, if the objects are chemical compounds, evaluation properties can be physical, chemical and/or biological properties associated with a set of chemical compounds. Under this formalism, the objects can be represented as vectors in multi-variate property space, and their similarity may be computed by some geometrical distance measure.

In an exemplary embodiment, the property space is defined using one or more features or descriptors. For the chemical compound example, the property space can be defined using one or more molecular features or descriptors. Such molecular features may include topological indices, physicochemical properties, electrostatic field parameters, volume and surface parameters, etc. These features can include, but are not limited to, molecular volume and surface areas, dipole moments, octanol-water partition coefficients, molar refractivities, heats of formation, total energies, ionization potentials, molecular connectivity indices, 2D and 3D auto-correlation vectors, 3D structural and/or pharmacophoric parameters, electronic fields, etc.

It should be understood, however, that the present invention is not limited to this embodiment. For example, molecular features may include the observed biological activities of a set of compounds against an array of biological targets such as enzymes or receptors (also known as affinity fingerprints). In fact, any vectorial representation of chemical data can be used in the present invention.

It should also be understood that the present invention is not limited to application with chemical compound objects. Instead, the present invention can be implemented with any data set or objects, including objects that are associated with evaluation properties that have continuous or discrete real values.

1. Relationships or Distance Measures Where Values of Evaluation Properties Are Continuous or Discrete Real Numbers A "distance measure" is some algorithm or technique used to determine a relationship between objects, based on selected evaluation properties. The particular distance measure that is used in any given situation depends, at least in part, on the set of values that the evaluation properties can take.

For example, where the evaluation properties can take real numbers as values, then a suitable distance measure is the Minkowski metric, shown in EQ. 14:

$$d_{ij} = d(x_i, x_j) = \left( \sum_k |x_{ik} - x_{jk}|^r \right)^{\frac{1}{r}} \qquad \text{EQ. 14}$$

where k is used to index the elements of the property vector, and r∈[1, ∞). For r=1.0, EQ. 14 is the city-block or Manhattan metric. For r=2.0, EQ. 14 is the ordinary Euclidean metric. For r=∞, EQ. 14 is the maximum of the absolute coordinate distances, also referred to as the 'dominance' metric, the 'sup' metric, or the 'ultrametric' distance. For any value of r∈[1, ∞), it can be shown that the Minkowski metric is a true metric, i.e. it obeys the distance postulates and, in particular, the triangle inequality.

B. Evaluation Properties Having Binary Values

Alternatively, the evaluation properties of the objects can be represented in a binary form, where bits are used to indicate the presence or absence, or potential presence or absence, of features or characteristics.

For example, if the objects are chemical compounds, the objects can be encoded using substructure keys where each bit denotes the presence or absence of a specific structural feature or pattern in the target molecule. Such features can include, but are not limited to, the presence, absence or minimum number of occurrences of a particular element (e.g. the presence of at least 1, 2 or 3 nitrogen atoms), unusual or important electronic configurations and atom types (e.g. doubly-bonded nitrogen or aromatic carbon), common functional groups such as alcohols, amines etc, certain primitive and composite rings, a pair or triplet of pharmacophoric groups at a particular separation in 3-dimensional space, and 'disjunctions' of unusual features that are rare enough not to worth an individual bit, yet extremely important when they do occur. Typically, these unusual features are assigned a common bit that is set if any one of the patterns is present in the target molecule.

Alternatively, evaluation properties of compounds may be encoded in the form of binary fingerprints, which do not depend on a predefined fragment or feature dictionary to perform the bit assignment. Instead, every pattern in the molecule up to a predefined limit is systematically enumerated, and serves as input to a hashing algorithm that turns 'on' a small number of bits at pseudo-random positions in the bitmap. Although it is conceivable that two different molecules may have exactly the same fingerprint, the probability of this happening is extremely small for all but the simplest cases. Experience suggests that these fingerprints contain sufficient information about the molecular structures to permit meaningful similarity comparisons.

1. Distance Measures Where Values of Evaluation Properties Are Binary

A number of relationship measures can be used with binary descriptors (i.e., where evaluation properties are binary or binary fingerprints). The most frequently used ones are the normalized Hamming distance:

$$H = \frac{|XOR(x, y)|}{N} \qquad \text{EQ. 15}$$

which measures the number of bits that are different between x and y, the Tanimoto or Jaccard coefficient:

$$T = \frac{|AND(x, y)|}{|IOR(x, y)|} \qquad \text{EQ. 16}$$

which is a measure of the number of substructures shared by two molecules relative to the ones they could have in common, and the Dice coefficient:

$$D = \frac{2|AND(x, y)|}{|x| + |y|} \qquad \text{EQ. 17}$$

In the equations listed above, AND(x, y) is the intersection of binary sets x and y (bits that are 'on' in both sets), IOR(x, y) is the union or 'inclusive or' of x and y (bits that are 'on' in either x or y), XOR is the 'exclusive or' of x and y (bits that are 'on' in either x or y, but not both), |x| is the number of bits that are 'on' in x, and N is the length of the binary sets measured in bits (a constant).

Another popular metric is the Euclidean distance which, in the case of binary sets, can be recast in the form:

$$E = \sqrt{N - |XOR(x, NOT(y))|} \qquad \text{EQ. 18}$$

where NOT(y) denotes the binary complement of y. The expression |XOR(x, NOT(y))| represents the number of bits that are identical in x and y (either 1's or 0's). The Euclidean distance is a good measure of similarity when the binary sets are relatively rich, and is mostly used in situations in which similarity is measured in a relative sense.

In the compound example, the distance between objects can be determined using a binary or multivariate representation. However, the present invention is not limited to this embodiment.

For example, the similarity between two compounds may be determined by comparing the shapes of the molecules using a suitable 3-dimensional alignment method, or it may be inferred by a similarity model defined according to a prescribed procedure. For example, one such similarity model may be a neural network trained to predict a similarity coefficient given a suitably encoded pair of compounds. Such a neural network may be trained using a training set of structure pairs and a known similarity coefficient for each such pair, as determined by user input, for example.

C. Scaling of Evaluation Properties

Referring back to EQ. 14, features (i.e., evaluation properties) may be scaled differently to reflect their relative importance in assessing the relationship between compounds. For example, a property A can be assigned a weight of 2, and a property B can be assigned a weight of 10. Property B will thus have five times more impact on the relationship calculation than Property A.

Accordingly, EQ. 14 can be replaced by EQ. 19:

$$d_{ij} = d(x_i, x_j) = \left( \sum_k (w_k |x_{ik} - x_{jk}|)^r \right)^{\frac{1}{r}} \qquad \text{EQ. 19}$$

where $w_k$ is the weight of the k-th property. An example of such a weighting factor is a normalization coefficient. However, other weighting schemes may also be used.

The scaling (weights) need not be uniform throughout the entire map, i.e. the resulting map need not be isomorphic. Hereafter, maps derived from uniform weights shall be referred to as globally weighted (isomorphic), whereas maps derived from non-uniform weights shall be referred to as locally weighted (non-isomorphic). On locally-weighted maps, the relationships (or distances) on the display map reflect a local measure of similarity. That is, what determines similarity in one domain of the display map is not necessarily the same with what determines similarity on another domain of the display map.

For example, locally-weighted maps may be used to reflect similarities derived from a locally-weighted case-based learning algorithm. Locally-weighted learning uses locally weighted training to average, interpolate between, extrapolate from, or otherwise combine training data. Most learning methods (also referred to as modeling or prediction methods) construct a single model to fit all the training data. Local models, on the other hand, attempt to fit the training data in a local region around the location of the query. Examples of local models include nearest neighbors, weighted average, and locally weighted regression. Locally-weighted learning is reviewed in Vapnik, in *Advances in Neural Information Processing Systems*, 4:831, Morgan-Kaufman, San Mateo, Calif. (1982); Bottou and Vapnik, *Neural Computation*, 4(6):888 (1992); and Vapnik and Bottou, *Neural Computation*, 5(6):893 (1993), all of which are incorporated herein by reference in their entireties.

Display maps can also be constructed from a relationship matrix that is not strictly symmetric, i.e. a relationship matrix where $r_{ij} \neq r_{ji}$. A potential use of this approach is in situations where a relationship (i.e., relationship function) is defined locally, for example, in a locally weighted model using a point-based local distance function. In this embodiment, each training case is associated with a distance function and the values of the corresponding parameters. Preferably, to construct a display map which reflects these local distance relationships, the distance between two points is evaluated twice, using the local distance functions of the respective points. The resulting distances are averaged, and are used as input in the display mapping algorithm described above. If the point-based local distance functions vary in some continuous or semi-continuous fashion throughout the feature space, this approach could potentially lead to a meaningful projection.

IX. Implementation of the Invention
A. Generally

Figure 6:
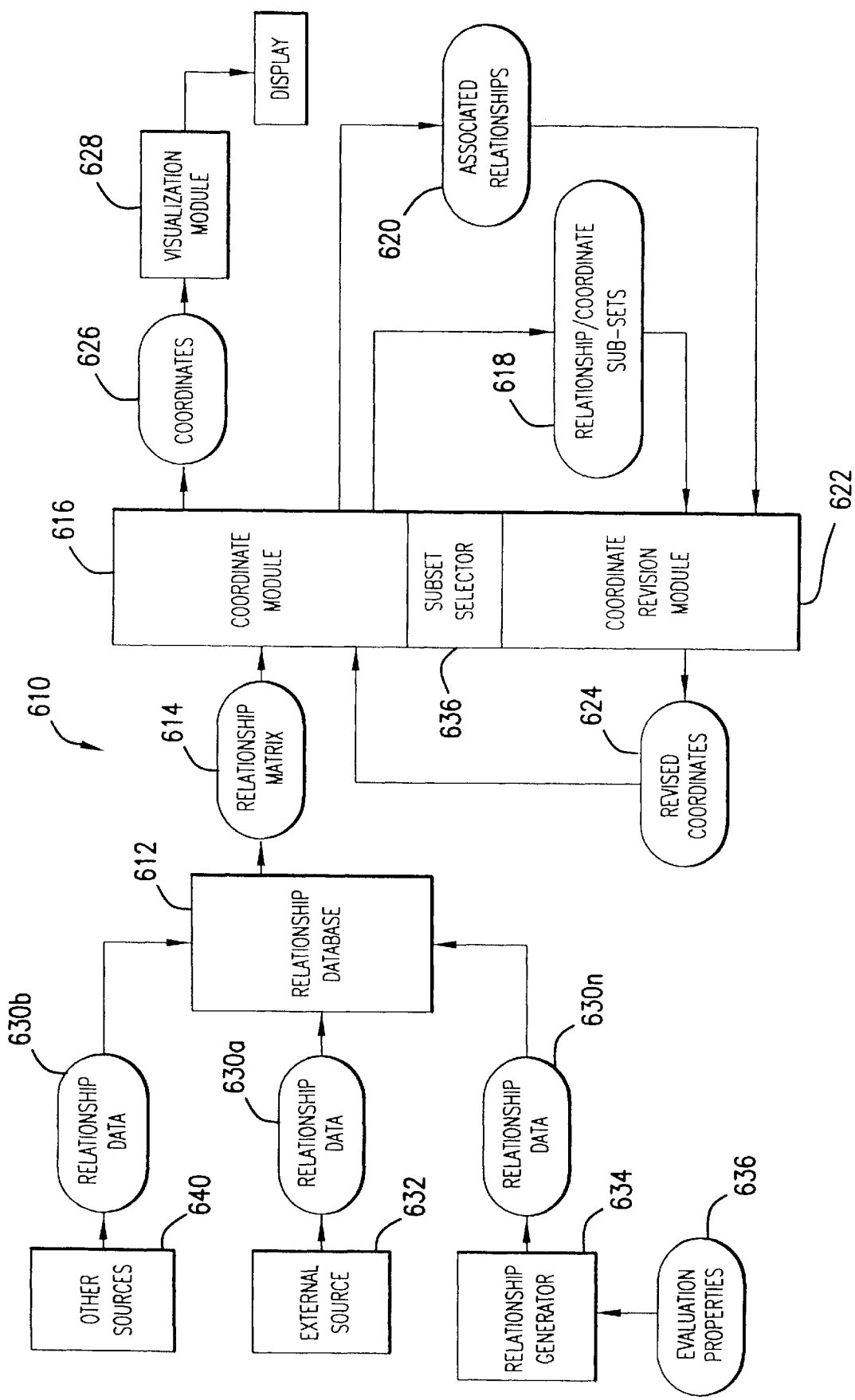
FIG. 6 is a block diagram of a system for representing relationships between objects.

The invention can be implemented in a variety of ways, using a variety of algorithms and can be implemented using hardware, software, firmware or any combination thereof. Referring to FIG. 6, an exemplary block diagram illustrates modules and data flow that can be included in a system 610 that implements the present invention. The block diagram of FIG. 6 is intended to aid in the understanding of the present invention. The present invention is not limited to the exemplary embodiment illustrated in the block diagram of FIG. 6.

System 610 includes a relational database 612 that stores relationship data 630 associated with objects. Types of data and associated relationships that can be accommodated by relational database 612 are without bounds, as the present invention can be implemented with any type of data for which relationships can be defined.

Relationship data 630 can be provided from one or more of a variety of sources. For example, relationship 630a can be provided by an external source 632, relationship 630b can be provided from other sources 640 and relationship data 630n can be generated by an optional relationship generator module 634, based upon evaluation properties 636. Optional relationship generator module 634 can include hardware, software, firmware or any combination thereof for executing one or more algorithms such as, for example, one or more of equations 14–19.

Relationship data 630 is provided to a coordinate module 616. In an exemplary embodiment, relationship 630 is provided to coordinated module 616 as a relationship matrix 614, which is preferably a matrix that stores any amount of relationship data 630 from the relationship database 612.

Coordinate module 616 assigns initial coordinates to data points or objects that are related by relationship data 630. The initial coordinates can be assigned at random or through any other technique. For example, the data can be pre-ordered or partially ordered. The coordinates comprise a display map. The display map can be a linear or display display map. The display map is an n-dimensional display map.

Relationship/coordinate sub-sets 618 and associated relationships 620 are provided to a coordinate revision module 622. In an exemplary embodiment, one relationship/coordinate sub-set 618 is provided to coordinate revision module 622 at a time.

A sub-set selector module 636 can be provided to select relationship/coordinate sub-sets 618 to be provided to coordinate revision module 622. Sub-set selector module 636 can select relationship/coordinate sub-sets 618 at random or through any other suitable method, including one or more of the methods described above.

Coordinate revision module 622 revises positions of the objects on the display map (i.e, revises coordinates 618) based on precise or imprecise measurements of similarity/dissimilarity (relationships 620). More specifically, coordinate revision module 622 measures distances between objects on the display map and compares them to associated relationships 620. Coordinate revision module 622 then revises coordinates 618 based on the comparisons. Such distances can be used directly, or to modify other display attributes.

Coordinate revision module 622 can include hardware, software, firmware or any combination thereof for executing one or more conventional multi-dimensional scaling or non-linear mapping algorithms as described above. In addition, or alternatively, coordinate revision module 622 can include hardware, software, firmware or any combination thereof for executing one or more novel algorithms for pair-wise analysis such as, for example, one or more of equations 8 through 13, or variations thereof.

When coordinate revision module 622 performs pair-wise analyses as described above, it can apply the learning rate $\lambda$ to ensure convergence of the distance between coordinates in relationship/coordinate sub-sets 618 and the associated relationship(s) 620. Coordinate revision module 622 can be designed to represent precise or imprecise measurements of similarity/dissimilarity (relationships 620). For example, coordinate revision module 622 can be programmed to handle complete pair-wise matrices that do not have uncertainties, sparse pair-wise matrices that do not have uncertainties, pair-wise matrices that include bounded uncertainties, and pair-wise matrices that include unbounded uncertainties (i.e., corrupt data), or any combination thereof. Coordinate revision module 622 can also be programmed to diffuse additional objects or data points into a set of objects, as described above.

Coordinate revision module 622 generates revised coordinates 624, which are returned to coordinate module 616. This process is repeated for additional sub-sets of coordinates 618 and associated relationships 620, and is preferably repeated on the same relationship/coordinate sub-sets 618 and associated relationships 620, until a prescribed tolerance or some other criteria is met.

In an exemplary embodiment, where visualization of the relationships between objects is desired, coordinates 626 can be provided to an optional visualization module 628 for display. As the iterative process of the invention continues, revised coordinates 626 are provided to optional visualization module 628.

B. Implementation of the Invention in a Computer Program Product

Figure 2:
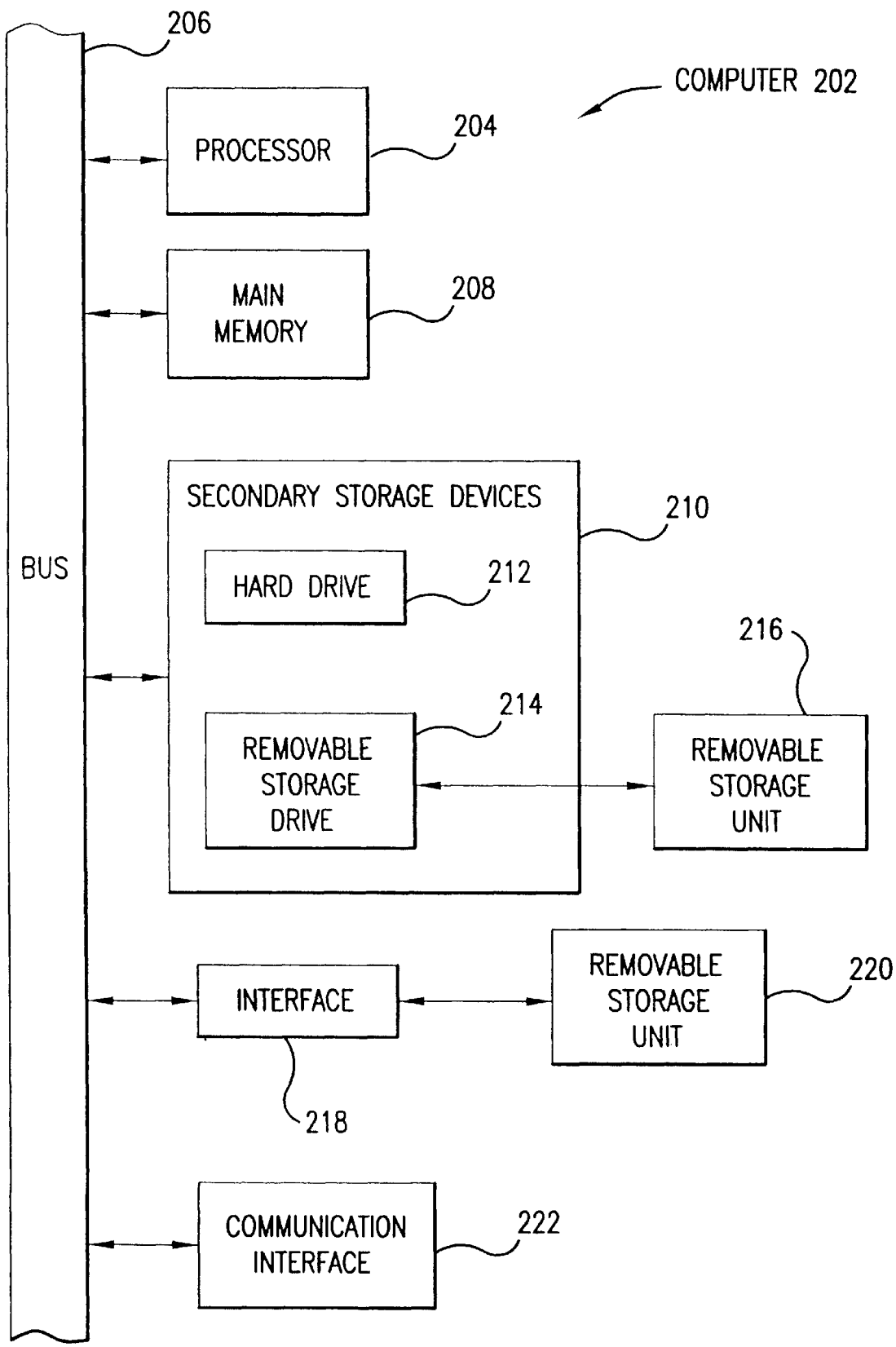
FIG. 2 is a block diagram of a computer useful for implementing components of the invention.

The present invention can be implemented using one or more computers. Referring to FIG. 2, an exemplary computer 202 includes one or more processors, such as processor 204. Processor 204 is connected to a communication bus 206. Various software embodiments are described in terms of this example computer system. After reading this description, it will become apparent to a person skilled in the relevant art(s) how to implement the invention using other computer systems and/or computer architectures.

Computer 202 also includes a main memory 208, preferably random access memory (RAM), and can also include one or more secondary storage devices 210. Secondary storage devices 210 can include, for example, a hard disk drive 212 and/or a removable storage drive 214, representing a floppy disk drive, a magnetic tape drive, an optical disk drive, etc. Removable storage drive 214 reads from and/or writes to a removable storage unit 216 in a well known manner. Removable storage unit 216 represents a floppy disk, magnetic tape, optical disk, etc., which is read by and written to by removable storage drive 214. Removable storage unit 216 includes a computer usable storage medium having stored therein computer software and/or data.

In alternative embodiments, the computer 202 can include other similar means for allowing computer programs or other instructions to be loaded into computer 202. Such means can include, for example, a removable storage unit 220 and an interface 218. Examples of such can include a program cartridge and cartridge interface (such as that found in video game devices), a removable memory chip (such as an EPROM, or PROM) and associated socket, and other removable storage units 220 and interfaces 218 which allow software and data to be transferred from the removable storage unit 220 to computer 202.

The computer 202 can also include a communications interface 222. Communications interface 222 allows software and data to be transferred between computer 202 and external devices. Examples of communications interface 222 include, but are not limited to a modem, a network interface (such as an Ethernet card), a communications port, a PCMCIA slot and card, etc. Software and data transferred via communications interface 222 are in the form of signals (typically data on a carrier) which can be electronic, electromagnetic, optical or other signals capable of being received by communications interface 222.

In this document, the term "computer program product" is used to generally refer to media such as removable storage units 216, 220, a hard drive 212 that can be removed from the computer 202, and signals carrying software received by the communications interface 222. These computer program products are means for providing software to the computer 202.

Computer programs (also called computer control logic) are stored in main memory and/or secondary storage devices 210. Computer programs can also be received via communications interface 222. Such computer programs, when executed, enable the computer 202 to perform the features of the present invention as discussed herein. In particular, the computer programs, when executed, enable the processor 204 to perform the features of the present invention. Accordingly, such computer programs represent controllers of the computer 202.

In an embodiment where the invention is implemented using software, the software can be stored in a computer program product and loaded into computer 202 using removable storage drive 214, hard drive 212, and/or communications interface 222. The control logic (software), when executed by the processor 204, causes the processor 204 to perform the functions of the invention as described herein.

In another embodiment, the automated portion of the invention is implemented primarily or entirely in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

The computer 202 can be any suitable computer, such as a computer system running an operating system supporting a graphical user interface and a windowing environment. A suitable computer system is a Silicon Graphics, Inc. (SGI) workstation/server, a Sun workstation/server, a DEC workstation/server, an IBM workstation/server, an IBM compatible PC, an Apple Macintosh, or any other suitable computer system, such as one using one or more processors from the Intel Pentium family, such as Pentium Pro or Pentium II. Suitable operating systems include, but are not limited to, IRIX, OS/Solaris, Digital Unix, AIX, Microsoft Windows 95/NT, Apple Mac OS, or any other operating system. For example, in an exemplary embodiment the program may be implemented and run on an Silicon Graphics Octane workstation running the IRIX 6.4 operating system, and using the Motif graphical user interface based on the X Window System.

C. Operation of the Present Invention

Figure 7:
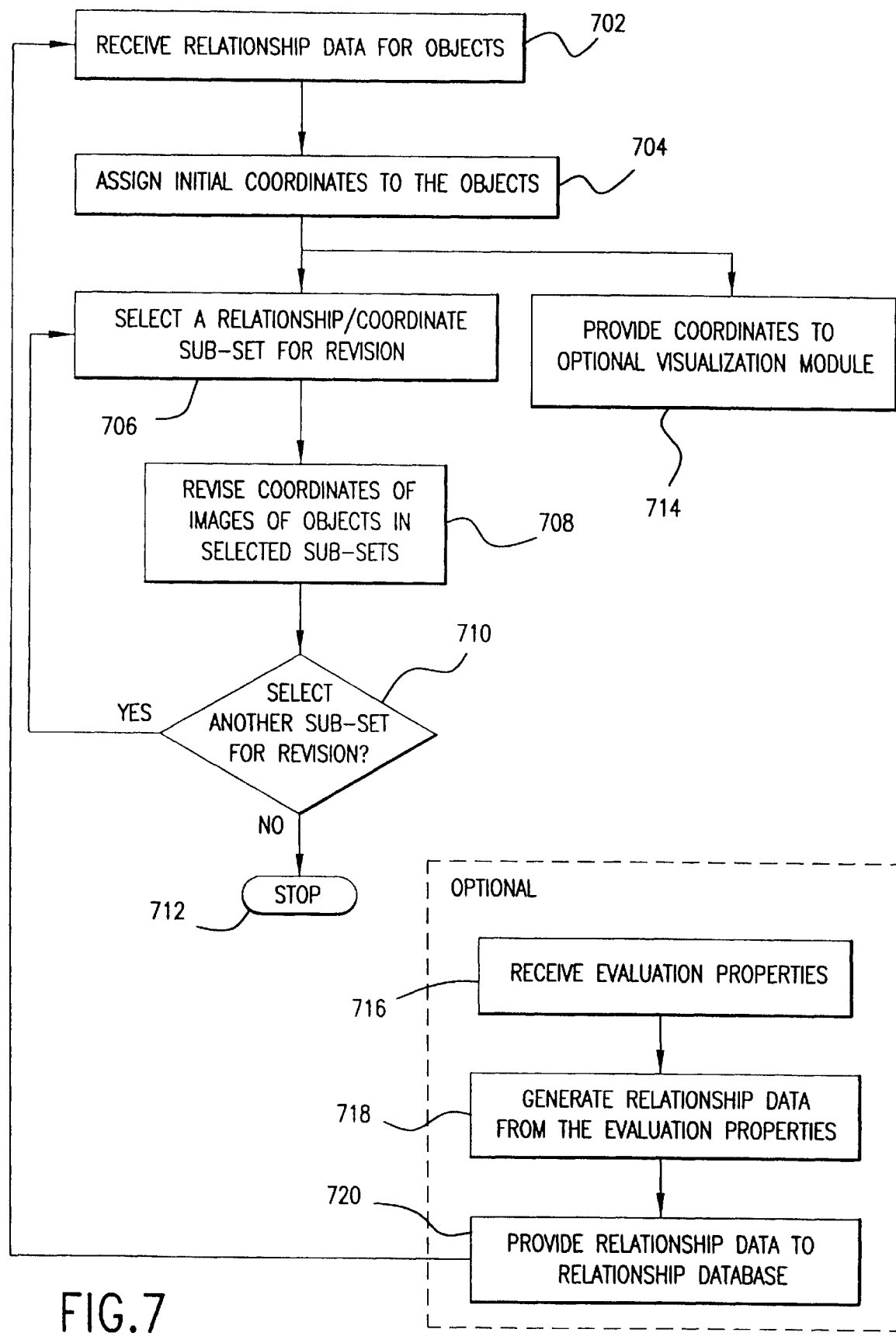
FIG. 7 is a process flowchart illustrating a method for representing relationships between objects.

Referring to FIG. 7, operation of the present invention is illustrated in a process flowchart 700. Operation of the present invention is illustrated for a general case where a relationship matrix 614 is a complete pair-wise relationship matrix without uncertainties. Based upon the descriptions above and process flowchart 700, one skilled in the relevant art(s) will be able to modify process flowchart 700 to accommodate other situations such as, for example: where a relationship matrix 614 is a sparse n-wise or pair-wise relationship matrix without uncertainties; where a relationship matrix 614 is a n-wise or pair-wise relationship matrix with bounded uncertainties; where a relationship matrix 614 is a pair-wise relationship matrix with unbounded uncertainties (i.e., corrupt data); etc.

The process for a general case where a relationship matrix 614 is a complete pair-wise relationship matrix without uncertainties begins at step 702, where coordinate module 616 receives relationship matrix 614 from relationship database 612.

In step 704, coordinate module 616 assigns initial coordinates to objects associated with relationships in relationship matrix 614. Assignment of initial coordinates can be done randomly. Alternatively, initial coordinates can be pre-ordered or partially pre-ordered.

In step 706, a relationship/coordinate sub-set 618 is selected from relationship matrix 614 for revision. Sub-set 618 can be selected randomly, semi-randomly, systematically, partially systematically, etc., by sub-set selector 638.

In step 708, the selected sub-set 618 and an associated relationship 620 are provided to coordinate revision module 622. Coordinate revision module 622 revises coordinates in relationship/coordinate sub-set 618, based upon the associated relationships 620.

In step 710, a determination is made whether to select another sub-set for coordinate revision. If another relationship/coordinate sub-set 618 is to be revised, processing returns to step 706 for selection of another relationship/coordinate sub-set 618. Otherwise, processing stops at step 712.

In an optional exemplary embodiment, coordinates 626 are provided in step 714 to optional visualization module 628 for display. Step 714 can be performed at any time during one or more of steps 706–1712.

In another optional exemplary embodiment, relationship data 630 is generated prior to step 702. In this optional exemplary embodiment, evaluation properties 636 are received in step 716. In step 718, relationship generator 634 generates relationship data 630 from the evaluation properties. In step 720, relationship data 630 is provided to relationship database 612.

Processing proceeds to step 702, where relationship data 630 is provided to coordinate module in the form of relationship matrix 614.

X. Example of the Invention

The present invention can be implemented in a variety of applications and with a variety of types of data. In an exemplary embodiment, the present invention can be implemented as a system, method, and/or computer program product for visualizing and interactively analyzing data relating to chemical compounds, where distances between objects in a multi-dimensional space represent similarities and/or dissimilarities of the corresponding compounds (relative to selected properties or features of the compounds) computed by some prescribed method. The resulting maps can be displayed on a suitable graphics device (such as a graphics terminal, for example), and interactively analyzed to reveal relationships between the data, and to initiate an array of tasks related to these compounds.

A user can select a plurality of compounds to map, and a method for evaluating similarity/dissimilarity between the selected compounds. A display map can be generated in accordance with the selected compounds and the selected method. The display map has a point for each of the selected compounds, wherein a distance between any two points is representative of similarity/dissimilarity between the corresponding compounds. A portion of the display map is then displayed. Users are enabled to interactively analyze compounds represented in the display map. Alternatively, all points can each correspond to multiple compounds or objects.

FIG. 1 is a block diagram of a computing environment 102 according to an exemplary embodiment of the present invention.

A chemical data visualization and interactive analysis module 104 includes a map generating module 106 and one or more auxiliary user interface components 108. The map generating module 106 determines similarities between chemical compounds relative to one or more selected properties or features (herein sometimes called evaluation properties or features) of the compounds. The map generating module 106 performs this function by retrieving and analyzing data on chemical compounds and reagents from one or more databases 120.

The chemical data visualization and interactive analysis module 104 communicates with the one or more databases 120 via a communication medium 118. The communication medium 118 is preferably any type of data communication means, such as a data bus, a computer network, etc.

The user interface modules 108 displays a preferably 2D or 3D display map on a suitable graphics device. The user interface modules 108 enable human operators to interactively analyze and process the information in the display map so as to reveal relationships between the data, and to initiate an array of tasks related to the corresponding compounds.

The user interface modules 108 enable users to organize compounds as collections (representing, for example, a combinatorial library). Information pertaining to compound collections are preferably stored in one or more databases 120.

Input Device(s) 114 receive input (such as data, commands, queries, etc.) from human operators and forward such input to, for example, the chemical data visualization and interactive analysis module 104 via the communication medium 118. Any well known, suitable input device can be used in the present invention, such as a keyboard, pointing device (mouse, roller ball, track ball, light pen, etc.), touch screen, voice recognition, etc. User input can also be stored and then retrieved, as appropriate, from data/command files.

Output Device(s) 116 output information to human operators. Any well known, suitable output device can be used in the present invention, such as a monitor, a printer, a floppy disk drive or other storage device, a text-to-speech synthesizer, etc.

Chemical data visualization and interactive analysis module 104 can interact with one or more computing modules 122 via the communication medium 118.

Components shown in the computing environment 102 of FIG. 1 (such as the chemical data visualization and interactive analysis module 104) can be implemented using one or more computers, such as an example computer 202 shown in FIG. 2.

A. Operation of the Exemplary Embodiment

Figure 3:
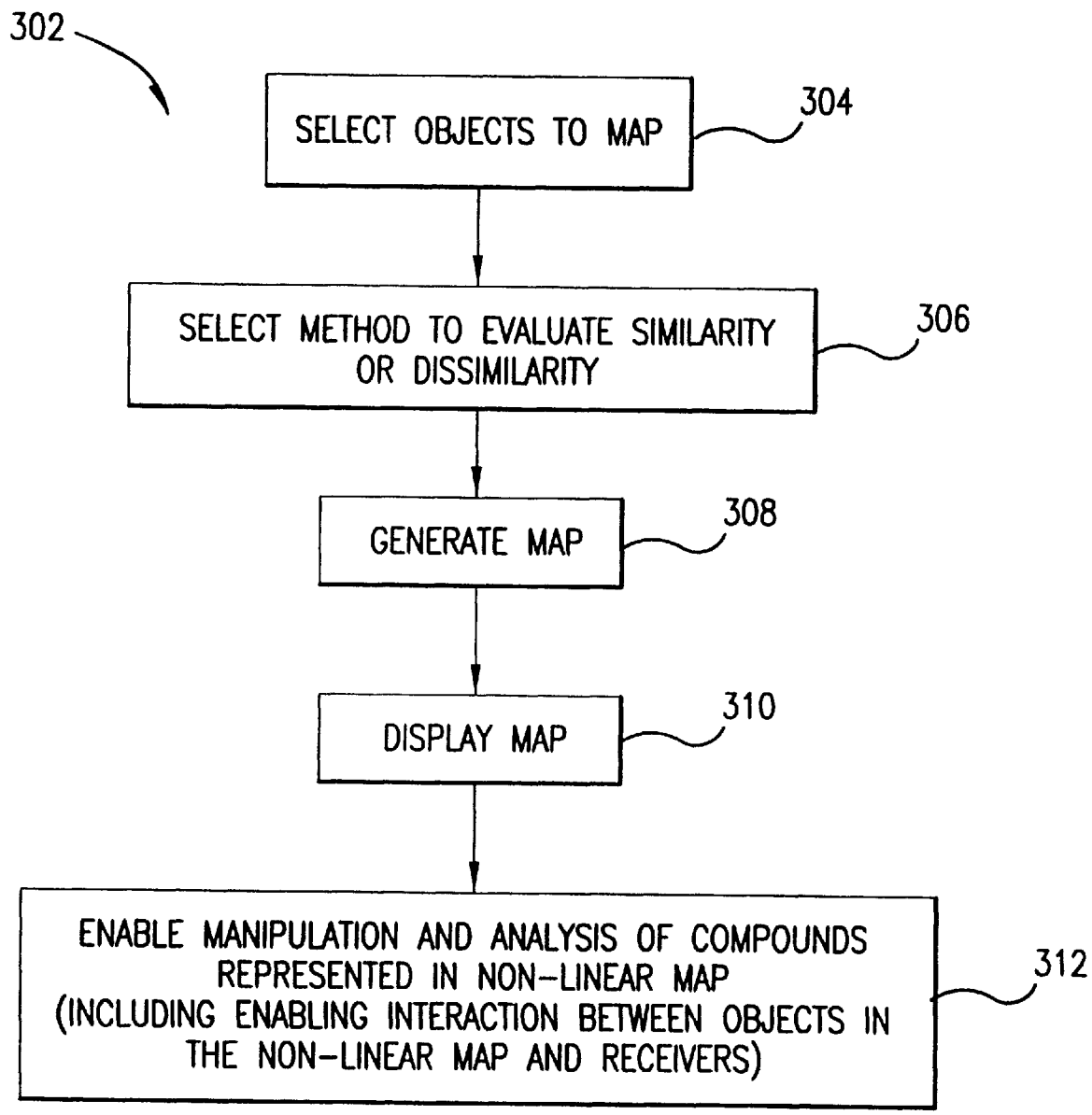
FIG. 3 is a flowchart representing the operation of the invention in visualizing and interactively processing display maps according to an embodiment of the invention.

The operation of the present invention as implemented for visualizing and interactively processing chemical compounds in a display map shall now be described with reference to a flowchart 302 shown in FIG. 3. Unless otherwise specified, interaction with users described below is achieved by operation of the user interface modules 108 (FIG. 1).

In step 304, the user selects one or more compounds to map in a new display map. The user may select compounds to map by retrieving a list of compounds from a file, by manually typing in a list of compounds, and/or by using a graphical user interface (GUI). The invention envisions other means for enabling the user to specify compounds to display in a display map.

In step 306, the user selects a method to be used for evaluating the molecular similarity or dissimilarity between the compounds selected in step 304. In an embodiment, the similarity/dissimilarity between the compounds selected in step 304 is determined (in step 308) based on a prescribed set of evaluation properties. As described above, evaluation properties can be any properties related to the structure, function, or identity of the compounds selected in step 304. Evaluation properties include, but are not limited to, structural properties, functional properties, chemical properties, physical properties, biological properties, etc., of the compounds selected in step 304.

In an embodiment of the present invention, the selected evaluation properties may be scaled differently to reflect their relative importance in assessing the proximity (i.e., similarity or dissimilarity) between two compounds. Accordingly, also in step 306, the user selects a scale factor for each of the selected evaluation properties. Note that such selection of scale factors is optional. The user need not select a scale factor for each selected evaluation property. If the user does not select a scale factor for a given evaluation property, then that evaluation property is given a default scale factor, such as unity.

Alternatively in step 306, the user can elect to retrieve similarity/dissimilarity values pertaining to the compounds selected in step 304 from a source, such as a database. These similarity/dissimilarity values in the database were previously generated. In another embodiment, the user in step 306 can elect to determine similarity/dissimilarity values using any well-known technique or procedure.

Figure 4:
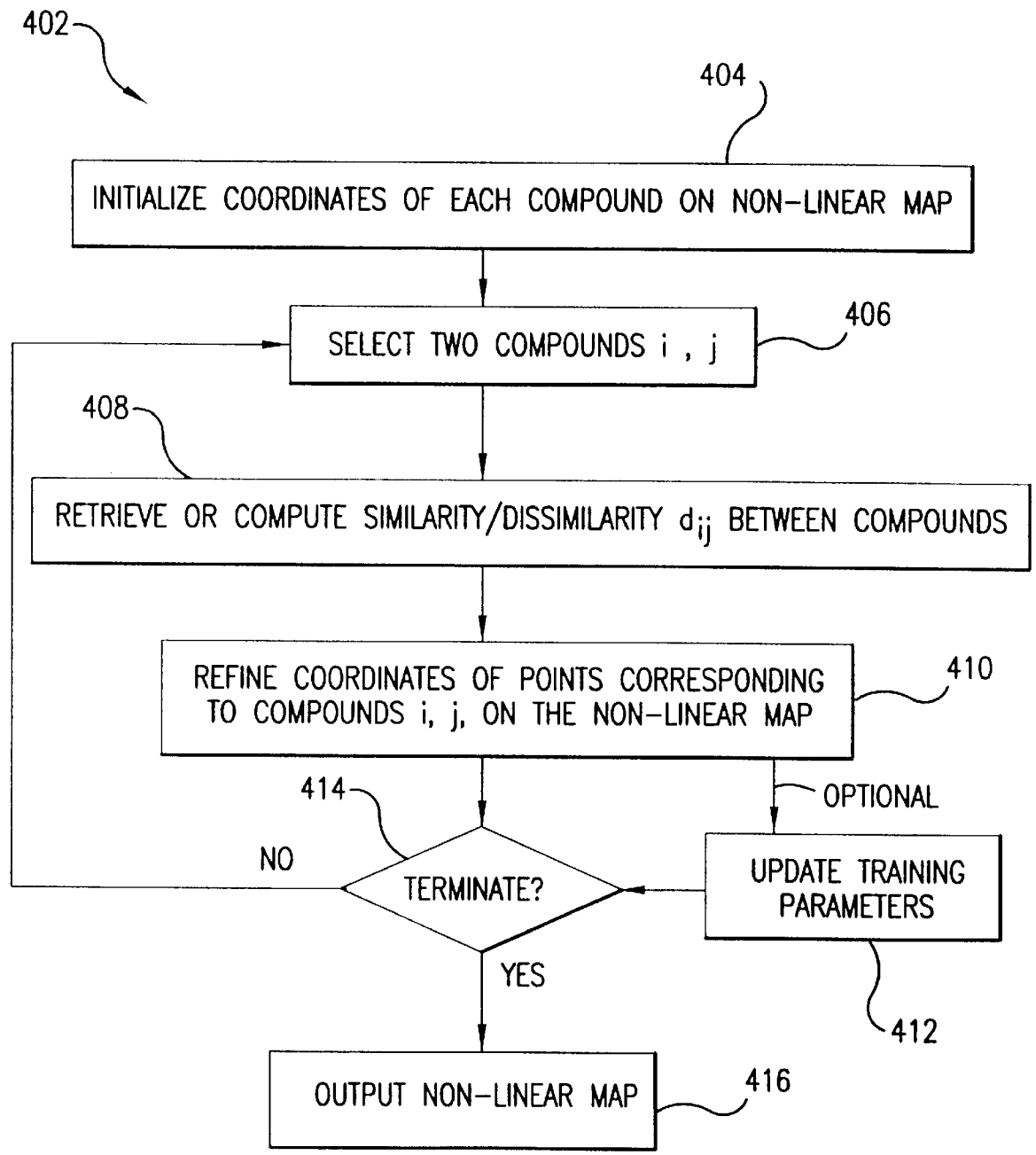
FIG. 4 is a flowchart representing the manner in which a display map is generated according to an embodiment of the invention.

In step 308, the map generating module 106 generates a new display map. This new display map includes a point for each of the compounds selected in step 304. Also, in this new display map, the distance between any two points is representative of the similarity/dissimilarity of the corresponding compounds. The manner in which the map generating module 106 generates the new display map shall now be further described with reference to a flowchart 402 in FIG. 4.

In step 404, coordinates on the new display map of points corresponding to the compounds selected in step 304 are initialized.

In step 406, two of the compounds i, j selected in step 304 are selected for processing.

In step 408, similarity/dissimilarity $r_{ij}$ between compounds i, j is determined based on the method selected by the user in step 306.

In step 410, based on the similarity/dissimilarity $r_{ij}$ determined in step 408, coordinates of points corresponding to compounds i, j on the display map are obtained.

In step 412, training/learning parameters are updated.

In step 414, a decision is made as to terminate or not terminate. If a decision is made to not terminate at this point, then control returns to step 406. Otherwise, step 416 is performed.

In step 416, the display map is output (i.e., generation of the display map is complete).

Details regarding the steps of flowchart 402 are discussed above. Referring again to FIG. 3, in step 312 the map viewer 112 displays the new display map on an output device 116 (such as a computer graphics monitor).

In step 314, the user interface modules 108 enable operators to interactively analyze and process the compounds represented in the displayed display map.

The present invention enables users to modify existing compound visualization display maps (as used herein, the term "compound visualization display map" refers to a rendered display map). For example, users can add additional compounds to the map, remove compounds from the map, highlight compounds on the map, etc. In such cases, pertinent functional steps of flowchart 302 are repeated. For example, steps 304 (selecting compounds to map), 310 (generating the display map), and 312 (displaying the map) are repeated when the user opts to add new compounds to an existing map. However, according to an embodiment of the invention, the map is incrementally refined and displayed in steps 310 and 312 when adding compounds to an existing compound visualization display map (this incremental refinement is described above).

The chemical compound example provided above is useful for visualizing and interactively processing any chemical entities including but not limited to (but can be used for) small molecules, polymers, peptides, proteins, etc. It may also be used to display different similarity relationships between these compounds.

XI. Conclusions

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention and would be apparent to persons skilled in the relevant art(s).

These functional building blocks may be implemented by discrete components, application specific integrated circuits, processors executing appropriate software and the like or any combination thereof. It is well within the scope of one skilled in the relevant art(s) to develop the appropriate circuitry and /or software to implement these functional building blocks.

Based on the above descriptions and examples, a person skilled in the relevant art(s) will be able to implement the present invention in a wide variety of applications, all of which fall within the scope of the invention.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A computerized method for generating mapping coordinates, wherein one or more pairs of objects are related by associated pair-wise relationships with bounded uncertainties, the method comprising the steps of:

(1) placing a set of objects on a display map;

(2) selecting a sub-set of objects from the set of objects, wherein the sub-set of objects includes at least one associated relationship between the objects in the sub-set;

(3) revising at least one distance between the objects on the display map based on the at least one associated relationship and the at least one distance, only when the at least one distance falls outside a set of allowable ranges of relationship values;

(4) repeating steps (2) and (3) for additional sub-sets of objects from the set of objects; and (5) generating mapping coordinates for the set of objects.

2. The method according to claim 1, wherein step (2) comprises the step of:

selecting a pair of objects having an associated pair-wise relationship.

3. The method according to claim 1, wherein the associated pair-wise relationships between one or more pairs of objects are unknown, the method further comprising the steps of:

performing steps (2) through (4) only for pairs of objects for which an associated pair-wise relationship is known; and allowing distances between objects on the display map for which associated pair-wise relationships are not known to adapt during performance of steps (2) through (4).

4. The method according to claim 1, wherein step (3) comprises the step of:

revising the at least one distance based on a learning rate.

5. The method according to claim 1, wherein step (3) comprises the step of:

revising the at least one distance based on a fixed learning rate.

6. The method according to claim 1, wherein step (3) comprises the step of:

revising the at least one distance based on a variable learning rate.

7. The method according to claim 1, wherein step (3) comprises the step of:

revising the at least one distance based on a learning rate that is a function of the associated pair-wise relationship between the pair of objects.

8. The method according to claim 1, wherein step (3) comprises the step of:

revising the at least one distance based on a learning rate that is a function of at least one object of the pair of objects.

9. The method according to claim 1, wherein step (3) comprises the step of:

revising the at least one distance based on a learning rate that is a function of the selected pair of objects.

10. The method according to claim 1, wherein step (3) comprises the step of:

revising the at least one distance using a conventional multi-dimensional scaling technique.

11. The method according to claim 1, wherein step (3) comprises the step of:

revising the at least one distance using a conventional non-linear mapping technique.

12. The method according to claim 1, wherein step (3) comprises the steps of:
   computing an error function value using a conventional technique; and
   revising the at least one distance using a gradient descent procedure.

13. The method according to claim 1, wherein that the objects do not represent chemical objects.

14. A computerized method for generating mapping coordinates, wherein one or more pairs of objects are related by associated pair-wise relationships with bounded uncertainties, the method comprising the steps of:
   (1) placing a set of objects on a display map;
   (2) selecting a sub-set of objects from the set of objects, wherein the sub-set of objects includes at least one associated relationship between the objects in the sub-set;
   (3) revising at least one distance between the objects on the display map based on the at least one associated relationship and the at least one distance, only when the at least one distance falls above an upper limit of allowable relationship values;
   (4) repeating steps (2) and (3) for additional sub-sets of objects from the set of objects; and
   (5) generating mapping coordinates for the set of objects.

15. The method according to claim 14, wherein step (2) comprises the step of:
   selecting a pair of objects having an associated pair-wise relationship.

16. The method according to claim 14, wherein the associated pair-wise relationships between one or more pairs of objects are unknown, the method further comprising the steps of:
   performing steps (2) through (4) only for pairs of objects for which an associated pair-wise relationship is known; and
   allowing distances between objects on the display map for which associated pair-wise relationships are not known to adapt during performance of steps (2) through (4).

17. The method according to claim 14, wherein step (3) comprises the step of:
   revising the at least one distance based on a learning rate.

18. The method according to claim 14, wherein step (3) comprises the step of:
   revising the at least one distance based on a fixed learning rate.

19. The method according to claim 14, wherein step (3) comprises the step of:
   revising the at least one distance based on a variable learning rate.

20. The method according to claim 14, wherein step (3) comprises the step of:
   revising the at least one distance based on a learning rate that is a function of the associated pair-wise relationship between the pair of objects.

21. The method according to claim 14, wherein step (3) comprises the step of:
   revising the at least one distance based on a learning rate that is a function of at least one object of the pair of objects.

22. The method according to claim 14, wherein step (3) comprises the step of:
   revising the at least one distance based on a learning rate that is a function of the selected pair of objects.

23. The method according to claim 14, wherein step (3) comprises the step of:
   revising the at least one distance using a conventional multi-dimensional scaling technique.

24. The method according to claim 14, wherein step (3) comprises the step of:
   revising the at least one distance using a conventional non-linear mapping technique.

25. The method according to claim 14, wherein step (3) comprises the steps of:
   computing an error function value using a conventional technique; and
   revising the at least one distance using a gradient descent procedure.

26. The method according to claim 14, wherein that the objects do not represent chemical objects.

27. A computerized method for generating mapping coordinates, wherein one or more pairs of objects are related by associated pair-wise relationships with bounded uncertainties, the method comprising the steps of:
   (1) placing a set of objects on a display map;
   (2) selecting a sub-set of objects from the set of objects, wherein the sub-set of objects includes at least one associated relationship between the objects in the sub-set;
   (3) revising at least one distance between the objects on the display map based on the at least one associated relationship and the at least one distance, only when the at least one distance falls below a lower limit of allowable relationship values;
   (4) repeating steps (2) and (3) for additional sub-sets of objects from the set of objects; and
   (5) generating mapping coordinates for the set of objects.

28. The method according to claim 27, wherein step (2) comprises the step of:
   selecting a pair of objects having an associated pair-wise relationship.

29. The method according to claim 27, wherein the associated pair-wise relationships between one or more pairs of objects are unknown, the method further comprising the steps of:
   performing steps (2) through (4) only for pairs of objects for which an associated pair-wise relationship is known; and
   allowing distances between objects on the display map for which associated pair-wise relationships are not known to adapt during performance of steps (2) through (4).

30. The method according to claim 27, wherein step (3) comprises the step of:
   revising the at least one distance based on a learning rate.

31. The method according to claim 27, wherein step (3) comprises the step of:
   revising the at least one distance based on a fixed learning rate.

32. The method according to claim 27, wherein step (3) comprises the step of:
   revising the at least one distance based on a variable learning rate.

33. The method according to claim 27, wherein step (3) comprises the step of:
   revising the at least one distance based on a learning rate that is a function of the associated pair-wise relationship between the pair of objects.

34. The method according to claim 27, wherein step (3) comprises the step of:

revising the at least one distance based on a learning rate that is a function of at least one object of the pair of objects.

35. The method according to claim 27, wherein step (3) comprises the step of:

revising the at least one distance based on a learning rate that is a function of the selected pair of objects.

36. The method according to claim 27, wherein step (3) comprises the step of:

revising the at least one distance using a conventional multi-dimensional scaling technique.

37. The method according to claim 27, wherein step (3) comprises the step of:

revising the at least one distance using a conventional non-linear mapping technique.

38. The method according to claim 27, wherein step (3) comprises the steps of:

computing an error function value using a conventional technique; and revising the at least one distance using a gradient descent procedure.

39. The method according to claim 27, wherein that the objects do not represent chemical objects.

40. A computerized method for generating mapping coordinates, wherein one or more pairs of objects are related by associated pair-wise relationships with unbounded uncertainties, the method comprising the steps of:

(1) placing a set of objects on a display map;

(2) identifying at least one pair of objects for which an associated pair-wise relationship contains an unbounded uncertainty;

(3) removing the associated pair-wise relationships with the unbounded uncertainties identified in step (2);

(4) selecting a sub-set of objects from the set of objects, wherein the sub-set of objects includes at least one associated relationship between the objects in the sub-set;

(5) revising at least one distance between the objects on the display map based on the at least one associated relationship and the at least one distance;

(6) repeating steps (4) and (5) for additional sub-sets of objects from the set of objects;

(7) allowing distances between the objects for which the associated pair-wise relationships have been removed to adapt during performance of steps (4) through (6); and (8) generating mapping coordinates for the set of objects.

41. The method according to claim 40, wherein step (4) comprises the step of:

selecting a pair of objects having an associated pair-wise relationship.

42. The method according to claim 40, wherein the associated pair-wise relationships between one or more pairs of objects are unknown, the method further comprising the steps of:

performing steps (4) through (6) only for pairs of objects for which an associated pair-wise relationship is known; and allowing distances between objects on the display map for which associated pair-wise relationships are not known to adapt during performance of steps (4) through (6).

43. The method according to claim 40, wherein step (5) comprises the step of:

revising the at least one distance based on a learning rate.

44. The method according to claim 40, wherein step (5) comprises the step of:

revising the at least one distance based on a fixed learning rate.

45. The method according to claim 40, wherein step (5) comprises the step of:

revising the at least one distance based on a variable learning rate.

46. The method according to claim 40, wherein step (5) comprises the step of:

revising the at least one distance based on a learning rate that is a function of the associated pair-wise relationship between the pair of objects.

47. The method according to claim 40, wherein step (5) comprises the step of:

revising the at least one distance based on a learning rate that is a function of at least one object of the pair of objects.

48. The method according to claim 40, wherein step (5) comprises the step of:

revising the at least one distance based on a learning rate that is a function of the selected pair of objects.

49. The method according to claim 40, wherein step (5) comprises the step of:

revising the at least one distance using a conventional multi-dimensional scaling technique.

50. The method according to claim 40, wherein step (5) comprises the step of:

revising the at least one distance using a conventional non-linear mapping technique.

51. The method according to claim 40, wherein step (5) comprises the steps of:

computing an error function value using a conventional technique; and revising the at least one distance using a gradient descent procedure.

52. The method according to claim 40, wherein that the objects do not represent chemical objects.

* * * * *